(12) United States Patent
McDonald et al.

(10) Patent No.: US 7,214,512 B2
(45) Date of Patent: May 8, 2007

(54) GENOMIC MAMMARY AMYLOID A SEQUENCE

(75) Inventors: Thomas L. McDonald, Lincoln, NE (US); Marilyn A. Larson, Lincoln, NE (US); Annika Weber, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 1020 days.

(21) Appl. No.: 10/116,788

(22) Filed: Apr. 4, 2002

(65) Prior Publication Data

US 2003/0170840 A1   Sep. 11, 2003
US 2006/0024804 A9   Feb. 2, 2006

Related U.S. Application Data

(63) Continuation-in-part of application No. PCT/US00/29065, filed on Oct. 20, 2000, and a continuation-in-part of application No. 09/425,679, filed on Oct. 22, 1999, now Pat. No. 6,509,444.

(60) Provisional application No. 60/218,611, filed on Jul. 17, 2000, provisional application No. 60/218,482, filed on Jul. 14, 2000.

(51) Int. Cl.
C12P 21/06 (2006.01)
C07H 17/00 (2006.01)
C07K 14/00 (2006.01)

(52) U.S. Cl. .................. 435/69.1; 435/252.3; 435/325; 435/320.1; 536/23.1; 530/350

(58) Field of Classification Search ............... 536/23.1; 435/69.1, 320.1, 252.3, 325; 530/350
See application file for complete search history.

(56) References Cited

U.S. PATENT DOCUMENTS

| | | | |
|---|---|---|---|
| 4,377,569 A | 3/1983 | Plymate |
| 4,425,330 A | 1/1984 | Norcross et al. |
| 4,755,380 A | 7/1988 | Grubb |
| 4,952,496 A | 8/1990 | Studier |
| 5,227,301 A | 7/1993 | Turner et al. |
| 5,536,640 A | 7/1996 | Sipe et al. |
| 5,585,098 A | 12/1996 | Coleman |
| 5,700,465 A | 12/1997 | Tao et al. |
| 5,807,684 A | 9/1998 | Simmons |
| 5,853,985 A | 12/1998 | Salbaum |
| 5,952,313 A | 9/1999 | Carlson |
| 5,958,883 A | 9/1999 | Snow |
| 6,004,936 A | 12/1999 | Kisilevsky |
| 6,013,857 A | 1/2000 | Deboer |

FOREIGN PATENT DOCUMENTS

| EP | 0872 558 | 10/1998 |
|---|---|---|
| EP | 1 067 194 | 1/2001 |
| WO | WO/95/21625 | 8/1995 |
| WO | WO/97/04317 | 2/1997 |
| WO | WO/97/06184 | 2/1997 |
| WO | WO/98/03206 | 1/1998 |
| WO | WO/98/40506 | 9/1998 |
| WO | WO/99/18227 | 4/1999 |
| WO | WO 01 14580 | 3/2001 |
| WO | WO/01/31006 | 3/2001 |

OTHER PUBLICATIONS

Bauman, H., et al., "The acute phase response", IT Review, 1994 Elsevier Science Ltd., 0167-5699/94.

Hulten, C., et al., "The acute phase serum amyloid A protein (SAA) in the horse: isolation and characterization of three isoforms", Veterinary Immunology and Immunopathology 57(1997) 215-227.

Jensen, L., et al., "Regulation of serum amyloid A protein expression during the acute-phase response", Biochem J. (1998) 334:489-503.

Kho Y.J., et al., "Cloning and characterization of involution-specific genes from the bovine mammary gland" Database EMBL accession No. AF160867 'Online! Jun. 30, 2000.

Kho, Y.J., et al., GenBank Submission AAF77630, serum amyloid A protein [Bos tauru].

Liang, Jun-shan, et al., "Amino terminao region of acute phase, but not constitutive, serym amyloid A (apoSAA) specifically binds and transports cholesterol into aortic smooth muscle and HepG2 cells", Journal of Lipid Research (1996) 37:2109-2116.

Liepnieks, J., et al., "The primary structure of serum amyloid A protein in the rabbit: Comparison with serum amyloid A proteins in other species", J Lab Clin Med (1991) 118(6):570-576.

Malle, E., "Human serum amyloid A (SSA) protein: a prominent acute-phase reactant for clinical practice", European Journal of Clinical Investigation (1996) 26::427-435.

McDonald, T., et al., "A monoclonal antibody sandwich immunoassay for serum amyloid A (SAA) protein", J. of Immunological Methods, 144 (1991) 149-155.

Migita, K., et al., "Serum Amyloid A Protein Induces Production of Matrix Metalloproteinases by Human Synovial Fibroblasts", Laboratory Investigation, 78(5):535-539 (1998).

Mitchell, T., et al., "The acute phase reactant serum amyloid A (SAA3) is a novel substrate for degradation by the metalloproteinases collagenase and stromelysin", Biochem et Biophysica Acta. 1156 (1998) 245-254.

Mitchell, T.I., et al., "Serum Amyloid A (SAA3) Produced by Rabbit Synovial Fibroblasts Treated with Phorbol Esters or Interleukin 1 induces Synthesis of Collagenase and is Neutralized with Specific Antiserum", J. Clinical Investigation 87(4):1177-1185 (1991).

(Continued)

Primary Examiner—Karen Cochrane Carlson
(74) Attorney, Agent, or Firm—McKee, Voorhees & Sease, P.L.C.

(57) ABSTRACT

A genomic nucleotide sequence encoding Serum Amyloid A (SAA), isolated and purified from mammalian colostrum, is disclosed. Methods of use for the same in transgenic protocols is also disclosed.

20 Claims, 20 Drawing Sheets
(1 of 20 Drawing Sheet(s) Filed in Color)

OTHER PUBLICATIONS

Patel, H., "Human Serium Amyloid A has Cytokine-Like Properties", Scand. J. Immunol. 1998, 48:410-418.

Peristeris, P., "Effects of serum amyloid A protein on lymphocytes, HeLa, and MRC5 cells in culture", Biochem. Cell Biol., (1989) 67:365-370.

Rossevatn, K., et al., "The complete amino acid sequence of bovine serum amyloid protein A (SAA) and of subspecies of the tissue-deposited amyloid fibril protein A", Scand. J. Immunol. 35(2):217-24 (1992).

Sletten, K., "The Primary Structure of Equine Serum Amyloid A (SAA) Protein", Scand. J. Immunol. 30(1):117-122 (1989).

Smith, J., et al., "Comparison of Serum Amyloid A and C-Reactive Protein as Indicators of Lung Inflammation in Corticosteroid Treated and Non-Corticosteroid Treated Cystic Fibrosis Patients", Journal of Clinical Laboratory Analysis 6:219-224 (1992).

Smith, J., et al., "Production of serum amyloid A and C-reactive Protein by HepG2 cells stimulated with combinations of cytokines or monocyte conditioned media: the effects of prednisolone", Clin. exp. Immunol. (1992) 783.

Smith, J., et al., "Use of Ethanol-Eluted Hydrophobic Interaction Chromatography in the Purification of Serum Amyloid A", Protein Expression and Purification 2:158-161 (1991).

Steel, D., et al., "Expression and regulation of Constitutive and Acute Phase Serum Amyloid A mRNAs in Hepatic and Non-Hepatic Cell Lines", 1996, Blackwell Science Ltd., Scandinavian Journal of Immunology, 44:493-500.

Steel, D., et al., "The major acute phase reactants: C-reactive protein, serum amyloid P component and serum and amyloid A protein", Review, 1994 Elsevier Science Ltd, 0167-5699/94.

Thompson, D., et al., "The value of acute phase protein measurements in clinical practice", Ann Clin Biochem 1992, 29:123-131.

Uhlar, C., "Evolution of the Serum Amyloid A (SAA) Protein Superfamily", Genomics 19:228-235 (1994).

Urieli-Shoval, S., et al., "Widespread Expression of Serum Amyloid A in Histologically Normal Human Tissues: Predominant Localization of the Epithelium", The Journal of Histochemistry & Cytochemistry 46(12):1377-1384 (1998).

Zimlichman, S., "Serum amyloid A, an acute phase protein, inhibits platelet activation", Serum amyloid A and platelet activation, 116(2):180-186.

Benson et al., "A unique insertion in the primary structure of bovine amyloid AA protein", J. Lab ClinMed, vol. 113, pp. 67-72, 1989.

Hirvonen, et al., "Acute phase Response in Heifers with Experimentally Induce Mastitis", J. of Dairy Res., 63:351-360, 1996.

Huszenicza, et al., "Diagnostic value of certain mastitis markers in following up the clinical and bacteriological changes in pharmacotherapeutic studies", Acta Veterinaria Hungarica 45(4):409-416, 1997.

Kho et al., "Rapid Communication: Cloning of bovine serum amyloid A3 cDNA1", American Society of Animal Science, May 19, 2000.

Kluve-Beckerman et al., "Human serum amyloid A—Three Hepatic mRNAs and the corresponding proteins in one person", The Journal of Clinical Investigation, vol. 82, pp. 1670-1675, 1988.

Kluve-Beckerman et al., "Primary structures of dog and cat amyloid A proteins: comparison to Human AA", Comp. Biochem Physiol. B, vol. 94, pp. 175-183, 1989.

Kluve-Beckerman et al., "Sequence Analysis of a Third Human SAA gene", Database CAPLUS on STN, meeting abstract, 1991.

Larson et al., "Human serum amyloid A3 peptide enhances intestinal MUC3 expression and inhibits EPEC adherence", pp. 531-540, Biochemical and Biophysical Research Communications 300, Elsevier Science, 2002.

Larson et al., "Induction of human mammary-associated serum amyloid A3 expression by prolactin od lipopolysaccharide", pp. 1030-1037, Biochemical and Biophysical Research Communications 301, Elsevier Science, 2003.

McDonald et al., "Elevated extrahepatic expression and secretion of mammary-associate serum amyloid A3 (M-SAA3) into colostrums", Veterinary Immunology and Immunopathology 6528, 2001.

Marhaug et al., "Mink serum amyloid A protein. Expression and primary structure based on cDNA", J. Biol. Chem., vol. 265, 10049-10054, 1990.

Newstead, D.F., Acceptable levels of bovine immunoglobin in colostrums testing:, New Zealand Journal of Dairy science and Technology, vol. 6, No. 2, p. 2, Xp008036075, 1971.

Nielsen et al., "Acute phase protein concentrations in serum and milk from healthy cows, coes with clinical mastitis and cows with extramammary inflammatory conditions", The Veterinary Record, vol. 154, No. 12, pp. 361-365, ISSN: 0042-4900, Mar. 20, 2004.

Rygg et al., "In vitro evaluation of an enhanced Human Serum Amyloid A (SAA) Promoter-regulated soluble TNF Receptor Fusion Protein for Anti-inflammatory Gene Therapy", Scand J Immunol, 2001.

Satoh, et al., "Sandwich Enzyme-linked immunosorbent assay for quantitative measurement of serum amyloid A protein in horses", Am. J. Vet Res. 56(10):1286-1291, 1995.

Schrodl et al., "C-reaction protein as a new parameter of mastitis's!", Tierarztlich Praxis, vol. 23, No. 4, pp. 337-341, XP008036085, ISSN: 0303-6286, 1995.

Sellar et al., "Organization of the Region Encompassing the Human Serum Amyloid A (SAA) Gene Famil on Chromosome 11", Genomics, vol. 23, pp. 492-495, 1994.

Sipe et al., "Direct binding enzyme-linked immunosorbent assay (Elisa) for serum amyloid A (SAA)", Journal of Immunological Methods, Elsevier Science, Publishers B.V. Amsterdam, NL, vol. 125, No. 1/2, pp. 125-135, XP002018648, ISSN: 0022-1759, 1989.

Sletten et al., "The amino acid sequence of an amyloid fibril protein AA isolated from the horse", Scand. Immunol. 26, 79-84, 1987.

Syversen et al., "The primary structure of serum amyloid A protein in the sheep, comparison with serum amyloid A in other species", Scand. J. Immuno., vol. 39, pp. 88-94, 1994.

Taktak, et al., "A solid phase enzyme immunoassay for serum amyloid A (SAA) Protein", J. Immun. Methods, 136:11-16, 1991.

Waalen et al., "The primary structure of amyloid fibril protein AA in endotoxin-induced amyloid", European Journal of Biochem, vol. 104, p. 407-412, 1980.

Wilkins, et al., "Rapid automated enzyme immunoassay of serum amyloid A", Clinical Chemistry 40(7):1284-1290, 1994.

Zank, et al., "Assessment of subacute mammary inflammation by soluble biomarkers in comparison to somatic cell counts in quarter milk samples from dairty cows", J. Vet. Med., 45:41-51, 1998.

| | | | | |
|---|---|---|---|---|
| COW colSAA (SEQ ID NO:1) | | | m wxtflkeagq | gakdmwray |
| SHEEP colSAA (SEQ ID NO:2) | | | w lltflkeag | |
| HORSE colSAA (SEQ ID NO:3) | | | re wftfl | |
| HORSE colSAA (SEQ ID NOs:4-8) | | | re lktflkeagq | g |
| RABBIT SAA3 | mklsigiifc | flilgvnsre | wltflkeagq | gakdmwrays |
| HORSE SAA | | | llsflgeaar | gtwdmirayn |
| MINK SAA1 | mklftglifc | slvlgvssq. | wysfigeavq | gawdmyrays |
| | 1 | | | |

| | | | | |
|---|---|---|---|---|
| HORSE colSAA | eanyiga | dkyfh | gny daaqrgpgga | |
| RABBIT SAA3 | dmkeanykns | dkyfhargny | daakrgpggv | waaevisdar |
| HORSE SAA | dmreanyiga | dkyfhargny | daakrgpgga | waakvisdar |
| MINK SAA1 | dmreanykns | dkyfhargny | daaqrgpgga | waakvisdar |
| | 41 | | | |

| | | | | |
|---|---|---|---|---|
| HORSE colSAA | vtdlf | k | | sgkdpnh |
| RABBIT SAA3 | enyqklig........rgae | | dskadqeanq | wgrsgndpnh |
| HORSE SAA | enfqrftdrf | sfggsgrgae | dsradqaane | wgrsgkdpnh |
| MINK SAA1 | ersqrvtdlf | kygdsghgve | dskadqaane | wgrsgkdpnh |
| | 81 | | | |

| | |
|---|---|
| HORSE colSAA | frphglpdky |
| RABBIT SAA3 | frpkglpdky |
| HORSE SAA | frphglpdky |
| MINK SAA1 | frpsglpdky |
| | 121 |

*Fig. 1*

```
                                                                    ▼
M  N  L  S  T  G  I  I  F  C  F  L  I  L  G  V  S  S  Q  R
ATGAACCTTTCCACGGGCATCATTTTCTGCTTCCTGATCCTGGGCGTCAGCAGCCAGAGA 60
TACTTGGAAAGGTGCCCGTAGTAAAAGACGAAGGACTAGGACCCGCAGTCGTCGGTCTCT

W  G  T  F  L  K  E  A  G  Q  G  A  K  D  M  W  R  A  Y  Q
TGGGGGACATTCCTCAAGGAAGCTGGTCAAGGGGCTAAAGACATGTGGAGAGCTTACCAA 120
ACCCCCTGTAAGGAGTTCCTTCGACCAGTTCCCCGATTTCTGTACACCTCTCGAATGGTT

D  M  K  E  A  N  Y  R  G  A  D  K  Y  F  H  A  R  G  N  Y
GACATGAAAGAAGCCAACTACAGGGGTGCAGACAAATACTTCCACGCCCGTGGAAACTAT 180
CTGTACTTTCTTCGGTTGATGTCCCCACGTCTGTTTATGAAGGTGCGGGCACCTTTGATA

D  A  A  R  R  G  P  G  G  A  W  A  A  K  V  I  S  N  A  R
GACGCTGCCCGAAGGGGACCTGGGGGTGCCTGGGCTGCTAAAGTGATCAGTAACGCCAGA 240
CTGCGACGGGCTTCCCCTGGACCCCCACGGACCCGACGATTTCACTAGTCATTGCGGTCT

E  T  I  Q  G  I  T  D  P  L  F  K  G  M  T  R  D  Q  V  R
GAGACTATTCAGGGAATCACAGACCCTCTGTTTAAGGGTATGACCAGGGACCAGGTACGG 300
CTCTGATAAGTCCCTTAGTGTCTGGGAGACAAATTCCCATACTGGTCCCTGGTCCATGCC

E  D  S  K  A  D  Q  F  A  N  E  W  G  R  S  G  K  D  P  N
GAGGATTCGAAGGCCGACCAGTTTGCCAACGAATGGGGCCGGAGTGGCAAAGACCCCAAC 360
CTCCTAAGCTTCCGGCTGGTCAAACGGTTGCTTACCCCGGCCTCACCGTTTCTGGGGTTG

H  F  R  P  A  G  L  P  D  K  Y  *
CACTTCAGACCTGCTGGCCTGCCTGACAAGTACTGA 396
GTGAAGTCTGGACGACCGGACGGACTGTTCATGACT
```

*Fig. 2*

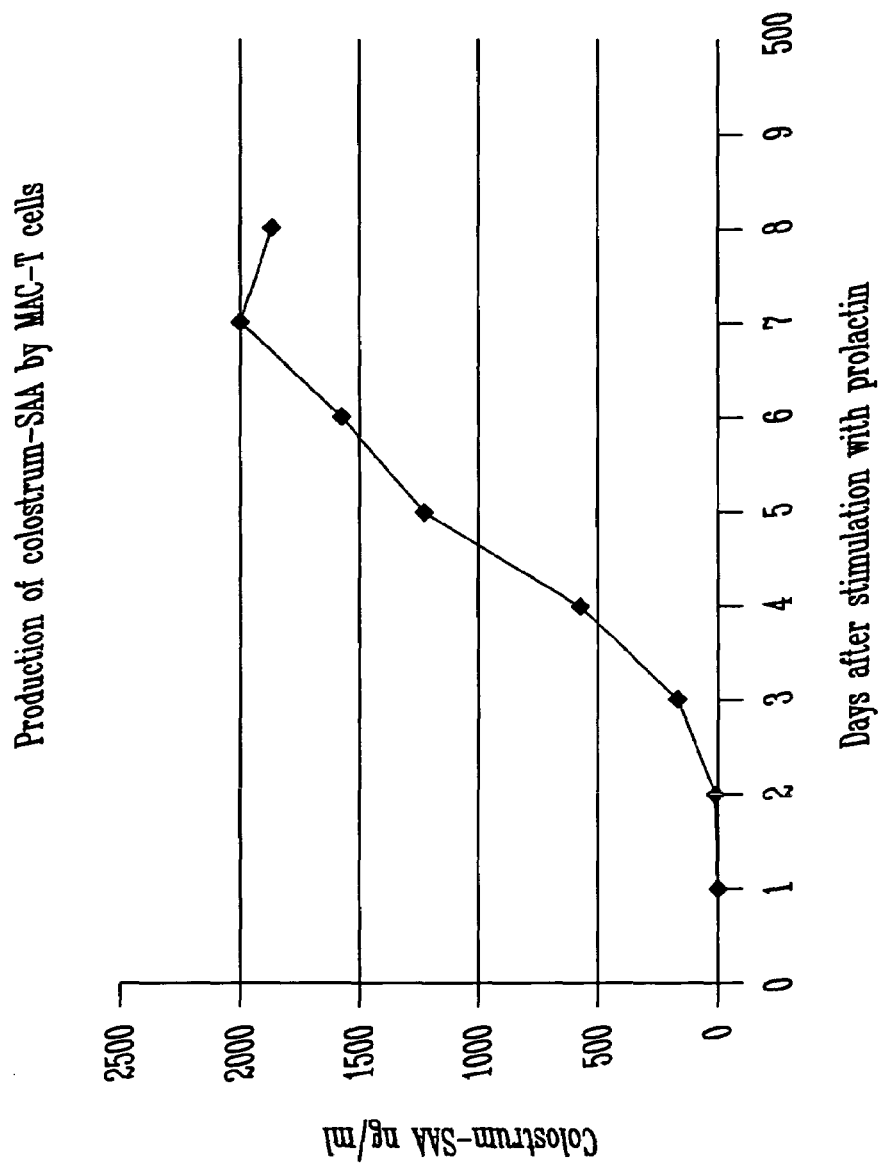

| Major Amino Acid | 2nd Amino Acid | 3rd Amino Acid |
|---|---|---|
| W | L |   |
| V | P | G |
| T | L |   |
| F | V | D/E |
| L | T | I |
| K |   | G |
| E | F | K |
| A | D | Q |
|   | P | V |

Fig. 5

MAC-T cell culture fluid with standards pH10　　pI 7.0　　pI 5.9　　pI 5.5　　pI 4.5　　pH3
Colostrum
SAA pI 9.4-9.6

MAC-T cell culture fluid pH10　Colostrum　　　　　　　　　　　　　　pH3
　　　SAA pI 9.4-9.6

Bovine Serum

Bovine Colostrum

"Milk Protein" TATA box                +1 (mRNA begins)
        GAGTATATAAAGCACCGGCCCCGTCTCCCAGGCAGGCAGCACAGGCAGCTCAGCTTCACC
    1   ---------+---------+---------+---------+---------+---------+  60
        CTCATATATTTCGTGGCCGGGGCAGAGGGTCCGTCCGTCGTGTCCGTCGAGTCGAAGTGG Intron 1 begins
                             ↓
        AGGAGCCTCAGCAGGAGGGCACGGCCACAGGTGAGGTGCTAGAACTCTCCAACACTTTTC
   61   ---------+---------+---------+---------+---------+---------+ 120
        TCCTCGGAGTCGTCCTCCCGTGCCGGTGTCCACTCCACGATCTTGAGAGGTTGTGAAAAG CTCTTCGGAGACTCTCTCTTCAGCAGCATTCTTGCGCTGCAGCCCAACTCTGCTTCCTTC
  121   ---------+---------+---------+---------+---------+---------+ 180
        GAGAAGCCTCTGAGAGAGAAGTCGTCGTAAGAACGCGACGTCGGGTTGAGACGAAGGAAG CTGAATCTACTGTTCTGACCATTAGAATCCACCAGATTGAGCACTTCAGGGAGTAGGGCT
  181   ---------+---------+---------+---------+---------+---------+ 240
        GACTTAGATGACAAGACTGGTAATCTTAGGTGGTCTAACTCGTGAAGTCCCTCATCCCGA CATCTTGTCTGCATCTTCTGTGCAGGCAGCGATGGGGTGAGCACGCAGGCCACAGACACA
  241   ---------+---------+---------+---------+---------+---------+ 300
        GTAGAACAGACGTAGAAGACACGTCCGTCGCTACCCCACTCGTGCGTCCGGTGTCTGTGT TGTGCCTCGTTCACCTCGTCTCGTATCACAGAGAGGCAGCATGAACACACTCCTCTTGCC
  301   ---------+---------+---------+---------+---------+---------+ 360
        ACACGGAGCAAGTGGAGCAGAGCATAGTGTCTCTCCGTCGTACTTGTGTGAGGAGAACGG TTTGGGAAACTTGCAGTGCAGCTGGGTCTCAGGGCTGATAGAGGATGACTGGACTGGAAA
  361   ---------+---------+---------+---------+---------+---------+ 420
        AAACCCTTTGAACGTCACGTCGACCCAGAGTCCCGACTATCTCCTACTGACCTGACCTTT GTGGTTTATGCTAAAAGCACGTTGCAATCCTTCACACAGGAAATCATTGGGATTCCAAGA
  421   ---------+---------+---------+---------+---------+---------+ 480
        CACCAAATACGATTTTCGTGCAACGTTAGGAAGTGTGTCCTTTAGTAACCCTAAGGTTCT TTTCATATGGAAATAAGAGCTGGATCCTCTGTGTTACAACCTATCGTCTGTCTACTGAGA
  481   ---------+---------+---------+---------+---------+---------+ 540
        AAAGTATACCTTTATTCTCGACCTAGGAGACACAATGTTGGATAGCAGACAGATGACTCT TAAAATTCAGAGGGGTTTATGTTCGGAATGTAAGAGTGTATCCACATTACAACTCAGCCC
  541   ---------+---------+---------+---------+---------+---------+ 600
        ATTTTAAGTCTCCCCAAATACAAGCCTTACATTCTCACATAGGTGTAATGTTGAGTCGGG

*Fig. 10A*

```
                                              Intron 1 ends
                                                   ↓
                                                   Start codon
         CAAGACCTGTCATTCTTGATTGACTCCGCTCATCTCTCTGTTGCAGGATGAACCTTTCCA
  601    ---------+---------+---------+---------+---------+---------+ 660
         GTTCTGGACAGTAAGAACTAACTGAGGCGAGTAGAGAGACAACGTCCTACTTGGAAAGGT

M   N   L   S   T

CGGGCATCATTTTCTGCTTCCTGATCCTGGGCGTCAGCAGCCAGAGATGGGGGACATTCC
  661    ---------+---------+---------+---------+---------+---------+ 720
         GCCCGTAGTAAAAGACGAAGGACTAGGACCCGCAGTCGTCGGTCTCTACCCCCTGTAAGG

Signal peptide cleavage site
                                                ▽
           G   I   I   F   C   F   L   I   L   G   V   S   S   Q   R   W   G   T   F   L Intron 2 begins
                  ↓
         TCAAGGAAGCTGGTCAAGGTAAGGACCAAAGGATGGGCCAGGGGAGGCTGTGTCTGCTTC
  721    ---------+---------+---------+---------+---------+---------+ 780
         AGTTCCTTCGACCAGTTCCATTCCTGGTTTCCTACCCGGTCCCCTCCGACACAGACGAAG

K   E   A   G   Q

CCCAGGATTGACCTGAGCAGAGGACACATCCCCACAGGGCAAAGGCCACAGGTGGGCAGA
  781    ---------+---------+---------+---------+---------+---------+ 840
         GGGTCCTAACTGGACTCGTCTCCTGTGTAGGGGTGTCCCGTTTCCGGTGTCCACCCGTCT

AAAGAAGCTTAGTTTTCATGGTAGCACTTCCCGAAGCTTTTCTGGCCAGCTTTGCACTCT
  841    ---------+---------+---------+---------+---------+---------+ 900
         TTTCTTCGAATCAAAAGTACCATCGTGAAGGGCTTCGAAAAGACCGGTCGAAACGTGAGA

TTTAGGGGATCCCCAAGCCCGAGGTCACATAAAGTTTGGGCCCCAACTTTCAGCAGGAGT
  901    ---------+---------+---------+---------+---------+---------+ 960
         AAATCCCCTAGGGGTTCGGGCTCCAGTGTATTTCAAACCCGGGGTTGAAAGTCGTCCTCA

GAGGAAGACATCTGGGGGGCAAGGTATCTGTTGCCAAAATACCAGTAAGGCTCTGCTACC
  961    ---------+---------+---------+---------+---------+---------+ 1020
         CTCCTTCTGTAGACCCCCCGTTCCATAGACAACGGTTTTATGGTCATTCCGAGACGATGG

GCCTCGTGGGCAACTAGAGATGGCTCATTTCCAAGTCTCCTGTAGCCATGAAGTGGGTGC
 1021    ---------+---------+---------+---------+---------+---------+ 1080
         CGGAGCACCCGTTGATCTCTACCGAGTAAAGGTTCAGAGGACATCGGTACTTCACCCACG

AACCGCTGAATACTTATAAATAAATACTTGATTTTTAGTAGCTGCCCAGGACTGTCTA
 1081    ---------+---------+---------+---------+---------+---------+ 1140
         TTGGCGACTTATGAATATTTATTTTATGAACTAAAAAATCATCGACGGGTCCTGACAGAT
```

*Fig. 10B*

```
      AGAGCTTTATATGCAGGAATCGACTCGTTTTCCCCCTCAGGGTTTAATCCTTGAGTCCTG
1141  ---------+---------+---------+---------+---------+---------+ 1200
      TCTCGAAATATACGTCCTTAGCTGAGCAAAAGGGGGAGTCCCAAATTAGGAACTCAGGAC

CAATGTAGGGACCATCACCCCTTATCAGAGAACCTGCTGCCCCAAGAGATTAAGATAGGG
1201  ---------+---------+---------+---------+---------+---------+ 1260
      GTTACATCCCTGGTAGTGGGGAATAGTCTCTTGGACGACGGGGTTCTCTAATTCTATCCC

TCCAACATCCTCCAGCAGAGCAGGATTGAACCCAGCATCCTGAGACCTTGCTGTTGACTT
1261  ---------+---------+---------+---------+---------+---------+ 1320
      AGGTTGTAGGAGGTCGTCTCGTCCTAACTTGGGTCGTAGGACTCTGGAACGACAACTGAA

CGGCCCTTCTACTGCCTCCCAGACAAGAGTACACGTGGAGGGTGAGGGGTCTGTGAACAC
1321  ---------+---------+---------+---------+---------+---------+ 1380
      GCCGGGAAGATGACGGAGGGTCTGTTCTCATGTGCACCTCCCACTCCCCAGACACTTGTG

GCATCCTGGTCTTTATCTGAGCAGATGGCAGAGAGTGGGGGTTGCTGCCTTTGGAAGGAA
1381  ---------+---------+---------+---------+---------+---------+ 1440
      CGTAGGACCAGAAATAGACTCGTCTACCGTCTCTCACCCCCAACGACGGAAACCTTCCTT

ACCCGATAGAGCTCCCCTCCCCACAGTAAATGGCAGCATGAGTTTCCTTGATGATGGTTC
1441  ---------+---------+---------+---------+---------+---------+ 1500
      TGGGCTATCTCGAGGGGAGGGGTGTCATTTACCGTCGTACTCAAAGGAACTACTACCAAG

TGCTGAGGCTGAGACCTGGCGAGAATCCTATAGCAAGAGATATAGACCTCACTAGCCAGA
1501  ---------+---------+---------+---------+---------+---------+ 1560
      ACGACTCCGACTCTGGACCGCTCTTAGGATATCGTTCTCTATATCTGGAGTGATCGGTCT

GCAAACTGGCCATAATTTATTTCCCAAAACTATTTGGTGTTATTATTTTTCTGTGATAAT
1561  ---------+---------+---------+---------+---------+---------+ 1620
      CGTTTGACCGGTATTAAATAAAGGGTTTTGATAAACCACAATAATAAAAGACACTATTA

TGCTGAATAATTGTTTTAAGCATTTGTTCTTAATTCCATCTAAATTCACACAGGCCCAGA
1621  ---------+---------+---------+---------+---------+---------+ 1680
      ACGACTTATTAACAAAATTCGTAAACAAGAATTAAGGTAGATTTAAGTGTGTCCGGGTCT

TAAAAGTATCTTTTCATCTCTTAGGTCAGTGTTGTTCAAGGGGCACTCTAGGATGACTTG
1681  ---------+---------+---------+---------+---------+---------+ 1740
      ATTTTCATAGAAAAGTAGAGAATCCAGTCACAACAAGTTCCCCGTGAGATCCTACTGAAC

CATGAGAATTAACCGTGGTCTGGGTGCTTTGTGGAATGCAGGTGCCTGGATCCACACACA
1741  ---------+---------+---------+---------+---------+---------+ 1800
      GTACTCTTAATTGGCACCAGACCCACGAAACACCTTACGTCCACGGACCTAGGTGTGTGT
```

*Fig. 10C*

```
      GTCCCTTCCCTGAACCACAGTCCCTGGGGCTGTCTGCAAATCTGTCCATTATTGAGCACC
1801  ---------+---------+---------+---------+---------+---------+  1860
      CAGGGAAGGGACTTGGTGTCAGGGACCCCGACAGACGTTTAGACAGGTAATAACTCGTGG

CCACTTGATTTTGTGCACAGTAAACACTGAGAACCACTACCTTGTTTTGCACCCAAGGGA
1861  ---------+---------+---------+---------+---------+---------+  1920
      GGTGAACTAAAACACGTGTCATTTGTGACTCTTGGTGATGGAACAAAACGTGGGTTCCCT

CAAATATGTCGTGCATTTGGAAGCACTTATTAAACAACTCTAGACTCCAGGGAACTATTT
1921  ---------+---------+---------+---------+---------+---------+  1980
      GTTTATACAGCACGTAAACCTTCGTGAATAATTTGTTGAGATCTGAGGTCCCTTGATAAA

AAATCTGTAACTCAGGGTGCATAGCTATAGTAAGAATATCATAGCCCTCAACCAAACTAT
1981  ---------+---------+---------+---------+---------+---------+  2040
      TTTAGACATTGAGTCCCACGTATCGATATCATTCTTATAGTATCGGGAGTTGGTTTGATA

TTTTCTGAACAGTGGAAATAGCTAACACCTAAAATAAAGATAAGTTATCTCATAGAGATA
2041  ---------+---------+---------+---------+---------+---------+  2100
      AAAAGACTTGTCACCTTTATCGATTGTGGATTTTATTTCTATTCAATAGAGTATCTCTAT

TTACATAAACTATTATTATAATCCATGTTATATTTTCCTCTTCCCTAATGAGCTAATCAT
2101  ---------+---------+---------+---------+---------+---------+  2160
      AATGTATTTGATAATAATATTAGGTACAATATAAAAGGAGAAGGGATTACTCGATTAGTA

TTAAACCTTTGCCATTTTATTCTATTTAGGTTGGGTTTTCTGTCCATGCCTCCCTGATCT
2161  ---------+---------+---------+---------+---------+---------+  2220
      AATTTGGAAACGGTAAAATAAGATAAATCCAACCCAAAAGACAGGTACGGAGGGACTAGA

CCATCCAACTTTATTTATTTTTTTGCCCTACTCTTCTAAGGACCAGAGAGGTGATAGTAT
2221  ---------+---------+---------+---------+---------+---------+  2280
      GGTAGGTTGAAATAAATAAAAAAACGGGATGAGAAGATTCCTGGTCTCTCCACTATCATA

AGTGAGCACCGACAATGTTCCATAAACTCAACCTGTATTTCCTCAGTTCTTCTGCATAAC
2281  ---------+---------+---------+---------+---------+---------+  2340
      TCACTCGTGGCTGTTACAAGGTATTTGAGTTGGACATAAAGGAGTCAAGAAGACGTATTG

CACCCTGAGGGAGGCATTACTCCTCCATTTTACTGGAGAGGACACTGAACTTTAGAGCTG
2341  ---------+---------+---------+---------+---------+---------+  2400
      GTGGGACTCCCTCCGTAATGAGGAGGTAAAATGACCTCTCCTGTGACTTGAAATCTCGAC

GTGGGTCAGTTGCCCTTTTTCTGCATCTGATTACCCTGTTTCTTCAAAGCCCTCTTAGGG
2401  ---------+---------+---------+---------+---------+---------+  2460
      CACCCAGTCAACGGGAAAAAGACGTAGACTAATGGGACAAAGAAGTTTCGGGAGAATCCC
```

*Fig. 10D*

```
       AGCTCACCTTTATCACCTGCTGATTTAATTCTGACGGTTGCCCATGTGCAAACATGCCCT
2461   ---------+---------+---------+---------+---------+---------+ 2520
       TCGAGTGGAAATAGTGGACGACTAAATTAAGACTGCCAACGGGTACACGTTTGTACGGGA

GAGTATTCAGATGTACTCAGGCCCGAGTTAGTCCCCAGGGCTGGATTTCTCCCCTTGACC
2521   ---------+---------+---------+---------+---------+---------+ 2580
       CTCATAAGTCTACATGAGTCCGGGCTCAATCAGGGGTCCCGACCTAAAGAGGGGAACTGG

AGCTGGGAGTATCCTATATCCACAGCCTTTCTCAGTATCGTCATTCTCAAGCTCTGATCA
2581   ---------+---------+---------+---------+---------+---------+ 2640
       TCGACCCTCATAGGATATAGGTGTCGGAAAGAGTCATAGCAGTAAGAGTTCGAGACTAGT

GAGCCTCTCCTGCGTCTTTCCAGGTGGAGGTTCATTGTATAAGCAAACATCCCTTAAAGA
2641   ---------+---------+---------+---------+---------+---------+ 2700
       CTCGGAGAGGACGCAGAAAGGTCCACCTCCAAGTAACATATTCGTTTGTAGGGAATTTCT

AAGCATTGACCGCTTCTTCACAGACATCACACACCTCCAGAAACAAAGTTCTAACAGACT
2701   ---------+---------+---------+---------+---------+---------+ 2760
       TTCGTAACTGGCGAAGAAGTGTCTGTAGTGTGTGGAGGTCTTTGTTTCAAGATTGTCTGA

TAGAATGAAATCAAACAGAATAAACCTTGCATCAAGTGTGATACTCACAACTTCAGATCA
2761   ---------+---------+---------+---------+---------+---------+ 2820
       ATCTTACTTTAGTTTGTCTTATTTGGAACGTAGTTCACACTATGAGTGTTGAAGTCTAGT

GGGAAGGAAGTGAGAAGTAAAGAAGTATTCATTTCAAGCCAATAAAATAATCTCCAAGGG
2821   ---------+---------+---------+---------+---------+---------+ 2880
       CCCTTCCTTCACTCTTCATTTCTTCATAAGTAAAGTTCGGTTATTTTATTAGAGGTTCCC

CTTGGTCGAAGGCTGAAACCTAAAATCAGTGGGAGGAAATGATTTATTTCTCTTTCACCA
2881   ---------+---------+---------+---------+---------+---------+ 2940
       GAACCAGCTTCCGACTTTGGATTTTAGTCACCCTCCTTTACTAAATAAAGAGAAAGTGGT

Intron 2 ends
                                                ↓
       AAACATGATCACATTCATATCATCATTTTCTTTTCTTCCCAGGGGCTAAAGACATGTGGA
2941   ---------+---------+---------+---------+---------+---------+ 3000
       TTTGTACTAGTGTAAGTATAGTAGTAAAAGAAAAGAAGGGTCCCCGATTTCTGTACACCT
                                                  G  A  K  D  M  W  R GAGCTTACCAAGACATGAAAGAAGCCAACTACAGGGGTGCAGACAAATACTTCCACGCCC
3001   ---------+---------+---------+---------+---------+---------+ 3060
       CTCGAATGGTTCTGTACTTTCTTCGGTTGATGTCCCCACGTCTGTTTATGAAGGTGCGGG

```
          GTGGAAACTATGACGCTGCCCGAAGGGGACCTGGGGGTGCCTGGGCTGCTAAAGTGATCA
3061      ---------+---------+---------+---------+---------+---------+ 3120
          CACCTTTGATACTGCGACGGGCTTCCCCTGGACCCCCACGGACCCGACGATTTCACTAGT

G   N   Y   D   A   A   R   R   G   P   G   G   A   W   A   A   K   V   I

Intron 3 begins
    ↓
          GGTACCAGGGTCCCTGGGGATGCAGGGATGGGTGAGCAGAGCTTGGCTGCCTAGGACAAC
3121      ---------+---------+---------+---------+---------+---------+ 3180
          CCATGGTCCCAGGGACCCCTACGTCCCTACCCACTCGTCTCGAACCGACGGATCCTGTTG CTGGAAGGGCNAAGCCTTGGAGAACTTTCCTGTAGGCTGTGNGCCCTCNTCCTCTTACCC
3181      ---------+---------+---------+---------+---------+---------+ 3240
          GACCTTCCCGNTTCGGAACCTCTTGAAAGGACATCCGACACNCGGGAGNAGGAGAATGGG ACCTTCCTGCTCTGTGCCCACTGTGAAGTCTGAGGGGCTGAAGAGCAGAGCAACTTGGTG
3241      ---------+---------+---------+---------+---------+---------+ 3300
          TGGAAGGACGAGACACGGGTGACACTTCAGACTCCCCGACTTCTCGTCTCGTTGAACCAC GGACAGGCGACTCTCCACCCTTNCTCTATGGGTGCTGTTCACCCAGCACAGGGCTGAGGT
3301      ---------+---------+---------+---------+---------+---------+ 3360
          CCTGTCCGCTGAGAGGTGGGAANGAGATACCCACGACAAGTGGGTCGTGTCCCGACTCCA GGGCTGAGCCTGAGGAGCCTCAGGGTTGTAGCCCCTCTTTCNTTGGCTCCTCTCAGAGTC
3361      ---------+---------+---------+---------+---------+---------+ 3420
          CCCGACTCGGACTCCTCGGAGTCCCAACATCGGGGAGAAAGNAACCGAGGAGAGTCTCAG ATTGATCCCTTGGAAAGAGGAGAGATGGGGAGGGTGGGGCTGTGGCTCATAGTCCTGGAT
3421      ---------+---------+---------+---------+---------+---------+ 3480
          TAACTAGGGAACCTTTCTCCTCTCTACCCCTCCCACCCCGACACCGAGTATCAGGACCTA Intron 3 ends
                                            ↓
          TAATCCCCTCCGTGCCCTCTTCCTTTCCAGTAACGCCAGAGAGACTATTCAGGGAATCAC
3481      ---------+---------+---------+---------+---------+---------+ 3540
          ATTAGGGGAGGCACGGGAGAAGGAAAGGTCATTGCGGTCTCTCTGATAAGTCCCTTAGTG

S   N   A   R   E   T   I   Q   G   I   T

AGACCCTCTGTTTAAGGGTATGACCAGGGACCAGGTACGGGAGGATTCGAAGGCCGACCA
3541      ---------+---------+---------+---------+---------+---------+ 3600
          TCTGGGAGACAAATTCCCATACTGGTCCCTGGTCCATGCCCTCCTAAGCTTCCGGCTGGT

```
            GTTTGCCAACGAATGGGGCCGGAGTGGCAAAGACCCCAACCACTTCAGACCTGCTGGCCT
     3601   ---------+---------+---------+---------+---------+---------+   3660
            CAAACGGTTGCTTACCCCGGCCTCACCGTTTCTGGGGTTGGTGAAGTCTGGACGACCGGA

F   A   N   E   W   G   R   S   G   K   D   P   N   H   F   R   P   A   G   L

Stop codon
            GCCTGACAAGTACTGAGCTGCCTCTCTCTCTGCTCAGGAGATGGGGCTGTGAGTCCCCAA
     3661   ---------+---------+---------+---------+---------+---------+   3720
            CGGACTGTTCATGACTCGACGGAGAGAGAGACGAGTCCTCTACCCCGACACTCAGGGGTT

P   D   K   Y   *

Polyadenylation signal
            GGACAGGGACACTGACCTAGAGAGTTCTCTGTCCTCAGAAGGAAGCAGATCTAATAAATG
     3721   ---------+---------+---------+---------+---------+---------+   3780
            CCTGTCCCTGTGACTGGATCTCTCAAGAGACAGGAGTCTTCCTTCGTCTAGATTATTTAC Probable site for cleavage and poly A(100-250) addition
                                ⇩
            CTTAAGAGATGGAATACTGAGACTGTGTGTCATTCTTGGTATAAGGACAGCCTGTTAGTT
     3781   ---------+---------+---------+---------+---------+---------+   3840
            GAATTCTCTACCTTATGACTCTGACACACAGTAAGAACCATATTCCTGTCGGACAATCAA CCAGGACTGATGGCCGGACACCGACGTGAAGGCTGAGCCTGTGCCTGTGTGTTTGGTTCT
     3841   ---------+---------+---------+---------+---------+---------+   3900
            GGTCCTGACTACCGGCCTGTGGCTGCACTTCCGACTCGGACACGGACACACAAACCAAGA GGCACACAATCTCAGCATCATTCAGGACAGACGCCCTCTGCAGCCTTCCCTAATCAGACC
     3901   ---------+---------+---------+---------+---------+---------+   3960
            CCGTGTGTTAGAGTCGTAGTAAGTCCTGTCTGCGGGAGACGTCGGAAGGGATTAGTCTGG CGCCCCCTCCCCAGACCCCTCTGGTGACACGGGGGCCATTTCCAGGCCCTTCACTGTCAG
     3961   ---------+---------+---------+---------+---------+---------+   4020
            GCGGGGGAGGGGTCTGGGGAGACCACTGTGCCCCCGGTAAAGGTCCGGGAAGTGACAGTC GCCTTCTCACTCCCTGCCGTTGTGTCCTGTCCCCTTCTCTGTCCCCAGGTCTAGTCCCCT
     4021   ---------+---------+---------+---------+---------+---------+   4080
            CGGAAGAGTGAGGGACGGCAACACAGGACAGGGGAAGAGACAGGGGTCCAGATCAGGGA AGCCTGTCCTCTGTGCTCTCTGTGTGGGGCATGGACACAGGAGGACTGGATGGTGGAATC
     4081   ---------+---------+---------+---------+---------+---------+   4140
            TCGGACAGGAGACACGAGAGACACACCCCGTACCTGTGTCCTCCTGACCTACCACCTTAG CTGCTCCAGAAACTGCCACCTGGATCTCCTGTTCATTTCTCAGCAGCACCTACAAGTACA
     4141   ---------+---------+---------+---------+---------+---------+   4200
            GACGAGGTCTTTGACGGTGGACCTAGAGGACAAGTAAAGAGTCGTCGTGGATGTTCATGT
```

*Fig. 10G*

```
       ACTATGAGCCAGTTTCTGTCTGTGCATCCGGAACTGCCTCCAGTGCTGTTCCCTTCCCTC
4201   ---------+---------+---------+---------+---------+---------+ 4260
       TGATACTCGGTCAAAGACAGACACGTAGGCCTTGACGGAGGTCACGACAAGGGAAGGGAG

TCTTTTCCTTGCCTTATACAAGTTCCCAGGAACAAACATGTCAAGGAGTGGAGGAATAAT
4261   ---------+---------+---------+---------+---------+---------+ 4320
       AGAAAAGGAACGGAATATGTTCAAGGGTCCTTGTTTGTACAGTTCCTCACCTCCTTATTA

GGCAACATGAAAATTCAGAGCCAGGCGCCTTTGTTTGCCTTGGATATGATTCATGTCCTC
4321   ---------+---------+---------+---------+---------+---------+ 4380
       CCGTTGTACTTTTAAGTCTCGGTCCGCGGAAACAAACGGAACCTATACTAAGTACAGGAG

GAGAGGAAGTCGTTTTCCCCTCCTGGTCCTTTCTCAACCCAGGGAAGCCAGCAGCAGTTA
4381   ---------+---------+---------+---------+---------+---------+ 4440
       CTCTCCTTCAGCAAAAGGGGAGGACCAGGAAAGAGTTGGGTCCCTTCGGTCGTCGTCAAT

CTTTTTATTGAGGAAAACAGTGTCTCTTATGGAAGGGAGTTGGGTCTGTTAGAGCACAGG
4441   ---------+---------+---------+---------+---------+---------+ 4500
       GAAAAATAACTCCTTTTGTCACAGAGAATACCTTCCCTCAACCCAGACAATCTCGTGTCC

AATTATGAGTGACTCTGTGAGTCATAACAATGCTGAATATGTAAACGCATACATACACAT
4501   ---------+---------+---------+---------+---------+---------+ 4560
       TTAATACTCACTGAGACACTCAGTATTGTTACGACTTATACATTTGCGTATGTATGTGTA

AAATAATGCACATGAATTATAGAGATTATGATAAAATAAAAATTGATAAATGTATCAGAA
4561   ---------+---------+---------+---------+---------+---------+ 4620
       TTTATTACGTGTACTTAATATCTCTAATACTATTTTATTTTTAACTATTTACATAGTCTT

CCACAAGCAGAAATTCATAATGGAAAATAAAAGGGTGTATCATGAATAAAGTCATAATGG
4621   ---------+---------+---------+---------+---------+---------+ 4680
       GGTGTTCGTCTTTAAGTATTACCTTTTATTTTCCCACATAGTACTTATTTCAGTATTACC

ATTCAGTAATCTTCATGTTCCATATTCCATCTGTTGTTGCTGTTGTTCAGTCACTCAGTC
4681   ---------+---------+---------+---------+---------+---------+ 4740
       TAAGTCATTAGAAGTACAAGGTATAAGGTAGACAACAACGACAACAAGTCAGTGAGTCAG

ATGTTGACTCTTAGGGACCCCATGGACTGCAGCATGCCAAGTTTCCCTGTCCTTCACTAT
4741   ---------+---------+---------+---------+---------+---------+ 4800
       TACAACTGAGAATCCCTGGGGTACCTGACGTCGTACGGTTCAAAGGGACAGGAAGTGATA

CACTTGGAGTTTGCTCAAACTCATGTCCATTGAGTCTGTGATGCCATTCAACCACCTCAT
4801   ---------+---------+---------+---------+---------+---------+ 4860
       GTGAACCTCAAACGAGTTTGAGTACAGGTAACTCAGACACTACGGTAAGTTGGTGGAGTA
```

*Fig. 10H*

```
       CCTCTGTGGCCTCCTTGTCCTCCTGCCGTCAGTCTTTCCCAGCGTAAGGGTCTTTTCCAG
4861   ---------+---------+---------+---------+---------+---------+ 4920
       GGAGACACCGGAGGAACAGGAGGACGGCAGTCAGAAAGGGTCGCATTCCCAGAAAAGGTC

TGAGTCAGCTGTTTGCAGCAGTTGGCTAAAGAATGGAGCTTCAGCATCAGTCTTTCCAAT
4921   ---------+---------+---------+---------+---------+---------+ 4980
       ACTCAGTCGACAAACGTCGTCAACCGATTTCTTACCTCGAAGTCGTAGTCAGAAAGGTTA

CAAT
4981   ---- 4984
       GTTA
```

*Fig. 10I*

```
                            SEQUENCE LISTING

<160> NUMBER OF SEQ ID NOS: 34

<210> SEQ ID NO 1
  <211> LENGTH: 20
  <212> TYPE: PRT
  <213> ORGANISM: Bos taurus
  <220> FEATURE:
  <221> NAME/KEY: misc_feature
  <222> LOCATION: 3
  <223> OTHER INFORMATION: X can be any amino acid

<400> SEQUENCE: 1

Met Trp Xaa Thr Phe Leu Lys Glu Ala Gly Gln Gly Ala Lys Asp Met
  1               5                   10                  15

Trp Arg Ala Tyr
              20

<210> SEQ ID NO 2
  <211> LENGTH: 10
  <212> TYPE: PRT
  <213> ORGANISM: Ovis aries

<400> SEQUENCE: 2

Trp Leu Leu Thr Phe Leu Lys Glu Ala Gly
  1               5                   10

<210> SEQ ID NO 3
  <211> LENGTH: 7
  <212> TYPE: PRT
  <213> ORGANISM: Equus caballus

<400> SEQUENCE: 3

Arg Glu Trp Phe Thr Phe Leu
  1               5

<210> SEQ ID NO 4
  <211> LENGTH: 13
  <212> TYPE: PRT
  <213> ORGANISM: Equus caballus

<400> SEQUENCE: 4

Arg Glu Leu Lys Thr Phe Leu Lys Glu Ala Gly Gln Gly
  1               5                   10

<210> SEQ ID NO 5
  <211> LENGTH: 12
  <212> TYPE: PRT
  <213> ORGANISM: Equus caballus

<400> SEQUENCE: 5

Glu Ala Asn Tyr Ile Gly Ala Asp Lys Tyr Phe His
  1               5                   10

<210> SEQ ID NO 6
  <211> LENGTH: 13
  <212> TYPE: PRT
```

-continued

<213> ORGANISM: Equus caballus

<400> SEQUENCE: 6

Gly Asn Tyr Asp Ala Ala Gln Arg Gly Pro Gly Gly Ala
1               5                   10

<210> SEQ ID NO 7
<211> LENGTH: 6
<212> TYPE: PRT
<213> ORGANISM: Equus caballus

<400> SEQUENCE: 7

Val Thr Asp Leu Phe Lys
1               5

<210> SEQ ID NO 8
<211> LENGTH: 17
<212> TYPE: PRT
<213> ORGANISM: Equus caballus

<400> SEQUENCE: 8

Ser Gly Lys Asp Pro Asn His Phe Arg Pro His Gly Leu Pro Asp Lys
1               5                   10                  15

Tyr

<210> SEQ ID NO 9
<211> LENGTH: 27
<212> TYPE: PRT
<213> ORGANISM: Oryctolagus cuniculus

<400> SEQUENCE: 9

Arg Glu Trp Leu Thr Phe Leu Lys Glu Ala Gln Gly Ala Lys Asp
1               5                   10                  15

Met Trp Arg Ala Tyr Ser Asp Met Lys Glu Ala
            20                  25

<210> SEQ ID NO 10
<211> LENGTH: 110
<212> TYPE: PRT
<213> ORGANISM: Equus caballus

<400> SEQUENCE: 10

Leu Leu Ser Phe Leu Gly Glu Ala Ala Arg Gly Thr Trp Asp Met Ile
1               5                   10                  15

Arg Ala Tyr Asn Asp Met Arg Glu Ala Asn Tyr Ile Gly Ala Asp Lys
            20                  25                  30

Tyr Phe His Ala Arg Gly Asn Tyr Asp Ala Ala Lys Arg Gly Pro Gly
                35                  40                  45

Gly Ala Trp Ala Ala Lys Val Ile Ser Asp Ala Arg Glu Asn Phe Gln
        50                  55                  60

Arg Phe Thr Asp Arg Phe Ser Phe Gly Gly Ser Gly Arg Gly Ala Glu
65                  70                  75                  80

Asp Ser Arg Ala Asp Gln Ala Ala Asn Glu Trp Gly Arg Ser Gly Lys
                85                  90                  95

Asp Pro Asn His Phe Arg Pro His Gly Leu Pro Asp Lys Tyr
            100                 105                 110

<210> SEQ ID NO 11
<211> LENGTH: 129
<212> TYPE: PRT
<213> ORGANISM: Mustela vison

<400> SEQUENCE: 11

```
Met Lys Leu Phe Thr Gly Leu Ile Phe Cys Ser Leu Val Leu Gly Val
1               5                   10                  15

Ser Ser Gln Trp Tyr Ser Phe Ile Gly Glu Ala Val Gln Gly Ala Trp
            20                  25                  30

Asp Met Tyr Arg Ala Tyr Ser Asp Met Arg Glu Ala Asn Tyr Lys Asn
        35                  40                  45

Ser Asp Lys Tyr Phe His Ala Arg Gly Asn Tyr Asp Ala Ala Gln Arg
    50                  55                  60

Gly Pro Gly Gly Ala Trp Ala Ala Lys Val Ile Ser Asp Ala Arg Glu
65                  70                  75                  80

Arg Ser Gln Arg Val Thr Asp Leu Phe Lys Tyr Gly Asp Ser Gly His
                85                  90                  95

Gly Val Glu Asp Ser Lys Ala Asp Gln Ala Ala Asn Glu Trp Gly Arg
            100                 105                 110

Ser Gly Lys Asp Pro Asn His Phe Arg Pro Ser Gly Leu Pro Asp Lys
        115                 120                 125

Tyr
```

<210> SEQ ID NO 12
<211> LENGTH: 396
<212> TYPE: DNA
<213> ORGANISM: Bos taurus
<220> FEATURE:
<221> NAME/KEY: CDS
<222> LOCATION: (1)..(396)
<223> OTHER INFORMATION:

<400> SEQUENCE: 12

```
atg aac ctt tcc acg ggc atc att ttc tgc ttc ctg atc ctg ggc gtc      48
Met Asn Leu Ser Thr Gly Ile Ile Phe Cys Phe Leu Ile Leu Gly Val
1               5                   10                  15 agc agc cag aga tgg ggg aca ttc ctc aag gaa gct ggt caa ggg gct      96
Ser Ser Gln Arg Trp Gly Thr Phe Leu Lys Glu Ala Gly Gln Gly Ala
            20                  25                  30 aaa gac atg tgg aga gct tac caa gac atg aaa gaa gcc aac tac agg     144
Lys Asp Met Trp Arg Ala Tyr Gln Asp Met Lys Glu Ala Asn Tyr Arg
        35                  40                  45 ggt gca gac aaa tac ttc cac gcc cgt gga aac tat gac gct gcc cga     192
Gly Ala Asp Lys Tyr Phe His Ala Arg Gly Asn Tyr Asp Ala Ala Arg
    50                  55                  60 agg gga cct ggg ggt gcc tgg gct gct aaa gtg atc agt aac gcc aga     240
Arg Gly Pro Gly Gly Ala Trp Ala Ala Lys Val Ile Ser Asn Ala Arg
65                  70                  75                  80 gag act att cag gga atc aca gac cct ctg ttt aag ggt atg acc agg     288
Glu Thr Ile Gln Gly Ile Thr Asp Pro Leu Phe Lys Gly Met Thr Arg
                85                  90                  95 gac cag gta cgg gag gat tcg aag gcc gac cag ttt gcc aac gaa tgg     336
Asp Gln Val Arg Glu Asp Ser Lys Ala Asp Gln Phe Ala Asn Glu Trp
            100                 105                 110 ggc cgg agt ggc aaa gac ccc aac cac ttc aga cct gct ggc ctg cct     384
Gly Arg Ser Gly Lys Asp Pro Asn His Phe Arg Pro Ala Gly Leu Pro
        115                 120                 125 gac aag tac tga                                                     396
Asp Lys Tyr
    130
```

<210> SEQ ID NO 13

-continued

```
<211> LENGTH: 131
<212> TYPE: PRT
<213> ORGANISM: Bos taurus

<400> SEQUENCE: 13

Met Asn Leu Ser Thr Gly Ile Ile Phe Cys Phe Leu Ile Leu Gly Val
1               5                   10                  15

Ser Ser Gln Arg Trp Gly Thr Phe Leu Lys Glu Ala Gly Gln Gly Ala
            20                  25                  30

Lys Asp Met Trp Arg Ala Tyr Gln Asp Met Lys Glu Ala Asn Tyr Arg
        35                  40                  45

Gly Ala Asp Lys Tyr Phe His Ala Arg Gly Asn Tyr Asp Ala Ala Arg
    50                  55                  60

Arg Gly Pro Gly Gly Ala Trp Ala Ala Lys Val Ile Ser Asn Ala Arg
65                  70                  75                  80

Glu Thr Ile Gln Gly Ile Thr Asp Pro Leu Phe Lys Gly Met Thr Arg
                85                  90                  95

Asp Gln Val Arg Glu Asp Ser Lys Ala Asp Gln Phe Ala Asn Glu Trp
            100                 105                 110

Gly Arg Ser Gly Lys Asp Pro Asn His Phe Arg Pro Ala Gly Leu Pro
        115                 120                 125

Asp Lys Tyr
    130

<210> SEQ ID NO 14
<211> LENGTH: 33
<212> TYPE: DNA
<213> ORGANISM: artificial sequence
<220> FEATURE:
<221> NAME/KEY: misc_feature
<223> OTHER INFORMATION: cDNA T-14 primer

<400> SEQUENCE: 14
gttgtcgact gtagtggagt tttttttttt ttt                            33

<210> SEQ ID NO 15
<211> LENGTH: 23
<212> TYPE: DNA
<213> ORGANISM: artificial sequence
<220> FEATURE:
<221> NAME/KEY: misc_feature
<223> OTHER INFORMATION: forward degenerate primer for colostrum
      associated SAA
<220> FEATURE:
<221> NAME/KEY: misc_feature
<222> LOCATION: 3, 9, 18, 21
<223> OTHER INFORMATION: n can be any nucleotide

<400> SEQUENCE: 15
acnttycyna argargcngg nca                                       23

<210> SEQ ID NO 16
<211> LENGTH: 24
<212> TYPE: DNA
<213> ORGANISM: artificial sequence
<220> FEATURE:
<221> NAME/KEY: misc_feature
<223> OTHER INFORMATION: reverse degenerate primer for colostrum
      associated SAA

<400> SEQUENCE: 16
gaagtgrttg gggtctttgc cact                                      24
```

<210> SEQ ID NO 17
<211> LENGTH: 8
<212> TYPE: PRT
<213> ORGANISM: artificial sequence
<220> FEATURE:
<221> NAME/KEY: misc_feature
<223> OTHER INFORMATION: amino terminal residues of colostrum SAA used
      to design primers

<400> SEQUENCE: 17

Thr Phe Leu Lys Glu Ala Gly Gln
1               5

<210> SEQ ID NO 18
<211> LENGTH: 8
<212> TYPE: PRT
<213> ORGANISM: artificial sequence
<220> FEATURE:
<221> NAME/KEY: misc_feature
<223> OTHER INFORMATION: carboxy terminal residues of colostrum SAA used
      to design primers

<400> SEQUENCE: 18

Ser Gly Lys Asp Pro Asn His Phe
1               5

<210> SEQ ID NO 19
<211> LENGTH: 27
<212> TYPE: DNA
<213> ORGANISM: artificial sequence
<220> FEATURE:
<221> NAME/KEY: misc_feature
<223> OTHER INFORMATION: forward primer for colostrum associated SAA

<400> SEQUENCE: 19
agcacaggca gctcagcttc accagga                                      27

<210> SEQ ID NO 20
<211> LENGTH: 35
<212> TYPE: DNA
<213> ORGANISM: artificial sequence
<220> FEATURE:
<221> NAME/KEY: misc_feature
<223> OTHER INFORMATION: reverse primer for colostrum associated SAA

<400> SEQUENCE: 20
gaagtatttg tctgcacccc tgtagttggc ttctt                             35

<210> SEQ ID NO 21
<211> LENGTH: 32
<212> TYPE: DNA
<213> ORGANISM: artificial sequence
<220> FEATURE:
<221> NAME/KEY: misc_feature
<223> OTHER INFORMATION: forward primer for colostrum associated SAA

<400> SEQUENCE: 21
ctgtttaagg gtatgaccag ggaccaggta cg                                32

<210> SEQ ID NO 22
<211> LENGTH: 19
<212> TYPE: DNA
<213> ORGANISM: artificial sequence
<220> FEATURE:
<221> NAME/KEY: misc_feature
<223> OTHER INFORMATION: cDNA-1 primer

<400> SEQUENCE: 22
gttgtcgact gtagtggag    19

<210> SEQ ID NO 23
<211> LENGTH: 27
<212> TYPE: DNA
<213> ORGANISM: artificial sequence
<220> FEATURE:
<221> NAME/KEY: misc_feature
<223> OTHER INFORMATION: forward degenerate primer used to amplify SAA
<220> FEATURE:
<221> NAME/KEY: modified_base
<222> LOCATION: (3)..(10)
<223> OTHER INFORMATION: m can be a or c
      y can be c or t

<400> SEQUENCE: 23
gacatgtggm gagcctactc ygacatg    27

<210> SEQ ID NO 24
<211> LENGTH: 9
<212> TYPE: PRT
<213> ORGANISM: artificial sequence
<220> FEATURE:
<221> NAME/KEY: misc_feature
<223> OTHER INFORMATION: sequence used to design primer for SAA

<400> SEQUENCE: 24

Asp Met Trp Arg Ala Tyr Ser Asp Met
1               5

<210> SEQ ID NO 25
<211> LENGTH: 8
<212> TYPE: PRT
<213> ORGANISM: artificial sequence
<220> FEATURE:
<221> NAME/KEY: misc_feature
<223> OTHER INFORMATION: sequence used to design SAA specific primer

<400> SEQUENCE: 25

Ser Gly Lys Asp Pro Asn His Phe
1               5

<210> SEQ ID NO 26
<211> LENGTH: 27
<212> TYPE: DNA
<213> ORGANISM: artificial sequence
<220> FEATURE:
<221> NAME/KEY: misc_feature
<223> OTHER INFORMATION: forward SAA primer

<400> SEQUENCE: 26
taagggtacg accagtggcc agggtca    27

<210> SEQ ID NO 27
<211> LENGTH: 10
<212> TYPE: PRT
<213> ORGANISM: artificial sequence
<220> FEATURE:
<221> NAME/KEY: misc_feature
<223> OTHER INFORMATION: sequence from SAA used to design primer

<400> SEQUENCE: 27

Phe Lys Gly Thr Thr Ser Gly Gln Gly Gln
1               5                   10

<210> SEQ ID NO 28
<211> LENGTH: 10
<212> TYPE: PRT

```
<213> ORGANISM: artificial sequence
<220> FEATURE:
<221> NAME/KEY: misc_feature
<223> OTHER INFORMATION: limited scramble for experiment

<400> SEQUENCE: 28

Met Trp Gly Leu Thr Lys Phe Glu Ala Gly
1               5                   10

<210> SEQ ID NO 29
<211> LENGTH: 10
<212> TYPE: PRT
<213> ORGANISM: artificial sequence
<220> FEATURE:
<221> NAME/KEY: misc_feature
<223> OTHER INFORMATION: randomized experimental control sequence

<400> SEQUENCE: 29

Gly Lys Phe Ala Trp Glu Gly Met Thr Leu
1               5                   10

<210> SEQ ID NO 30
<211> LENGTH: 10
<212> TYPE: PRT
<213> ORGANISM: artificial sequence
<220> FEATURE:
<221> NAME/KEY: misc_feature
<223> OTHER INFORMATION: N-terminal region of bovine colostrum SAA

<400> SEQUENCE: 30

Met Trp Gly Thr Phe Leu Lys Glu Ala Gly
1               5                   10

<210> SEQ ID NO 31
<211> LENGTH: 4984
<212> TYPE: DNA
<213> ORGANISM: Bos taurus
<220> FEATURE:
<221> NAME/KEY: misc_feature
<222> LOCATION: 3191, 3222, 3229, 3323, 3402
<223> OTHER INFORMATION: n can be a, t, c, or g

<400> SEQUENCE: 31
```

| | | | |
|---|---|---|---|
| gagtatataa agcaccggcc ccgtctccca ggcaggcagc acaggcagct cagcttcacc | 60 |
| aggagcctca gcaggagggc acggccacag gtgaggtgct agaactctcc aacactttc | 120 |
| ctcttcggag actctctctt cagcagcatt cttgcgctgc agcccaactc tgcttccttc | 180 |
| ctgaatctac tgttctgacc attagaatcc accagattga gcacttcagg gagtagggct | 240 |
| catcttgtct gcatcttctg tgcaggcagc gatggggtga gcacgcaggc cacagacaca | 300 |
| tgtgcctcgt tcacctcgtc tcgtatcaca gagaggcagc atgaacacac tcctcttgcc | 360 |
| tttgggaaac ttgcagtgca gctgggtctc agggctgata gaggatgact ggactggaaa | 420 |
| gtggtttatg ctaaaagcac gttgcaatcc ttcacacagg aaatcattgg gattccaaga | 480 |
| tttcatatgg aaataagagc tggatcctct gtgttacaac ctatcgtctg tctactgaga | 540 |
| taaaattcag aggggtttat gttcggaatg taagagtgta tccacattac aactcagccc | 600 |
| caagacctgt cattcttgat tgactccgct catctctctg ttgcaggatg aaccttttcca | 660 |
| cgggcatcat tttctgcttc ctgatcctgg gcgtcagcag ccagagatgg gggacattcc | 720 |
| tcaaggaagc tggtcaaggt aaggaccaaa ggatgggcca ggggaggctg tgtctgcttc | 780 |
| cccaggattg acctgagcag aggacacatc cccacagggc aaaggccaca ggtgggcaga | 840 |
| aaagaagctt agttttcatg gtagcacttc ccgaagcttt tctggccagc tttgcactct | 900 |

```
tttaggggat ccccaagccc gaggtcacat aaagtttggg ccccaacttt cagcaggagt    960
gaggaagaca tctgggggc aaggtatctg ttgccaaaat accagtaagg ctctgctacc   1020
gcctcgtggg caactagaga tggctcattt ccaagtctcc tgtagccatg aagtgggtgc   1080
aaccgctgaa tacttataaa taaaatactt gatttttag tagctgccca ggactgtcta   1140
agagctttat atgcaggaat cgactcgttt tccccctcag ggtttaatcc ttgagtcctg   1200
caatgtaggg accatcaccc cttatcagag aacctgctgc cccaagagat taagataggg   1260
tccaacatcc tccagcagag caggattgaa cccagcatcc tgagaccttg ctgttgactt   1320
cggcccttct actgcctccc agacaagagt acacgtggag ggtgagggt ctgtgaacac   1380
gcatcctggt ctttatctga gcagatggca gagagtgggg gttgctgcct ttggaaggaa   1440
acccgataga gctcccctcc ccacagtaaa tggcagcatg agtttccttg atgatggttc   1500
tgctgaggct gagacctggc gagaatccta tagcaagaga tatagacctc actagccaga   1560
gcaaactggc cataatttat ttcccaaaac tatttggtgt tattatttt ctgtgataat   1620
tgctgaataa ttgttttaag catttgttct taattccatc taaattcaca caggcccaga   1680
taaaagtatc ttttcatctc ttaggtcagt gttgttcaag gggcactcta ggatgacttg   1740
catgagaatt aaccgtggtc tgggtgcttt gtggaatgca ggtgcctgga tccacacaca   1800
gtcccttccc tgaaccacag tccctggggc tgtctgcaaa tctgtccatt attgagcacc   1860
ccacttgatt ttgtgcacag taaacactga gaaccactac cttgttttgc acccaaggga   1920
caaatatgtc gtgcatttgg aagcacttat taaacaactc tagactccag ggaactattt   1980
aaatctgtaa ctcagggtgc atagctatag taagaatatc atagccctca accaaactat   2040
ttttctgaac agtggaaata gctaacacct aaaataaaga taagttatct catagagata   2100
ttacataaac tattattata atccatgtta tattttcctc ttccctaatg agctaatcat   2160
ttaaaccttt gccattttat tctatttagg ttgggttttc tgtccatgcc tccctgatct   2220
ccatccaact ttatttattt ttttgcccta ctcttctaag gaccagagag gtgatagtat   2280
agtgagcacc gacaatgttc cataaactca acctgtattt cctcagttct tctgcataac   2340
caccctgagg gaggcattac tcctccattt tactggagag gacactgaac tttagagctg   2400
gtgggtcagt tgccctttt ctgcatctga ttaccctgtt tcttcaaagc cctcttaggg   2460
agctcacctt tatccctgc tgatttaatt ctgacggttg cccatgtgca aacatgccct   2520
gagtattcag atgtactcag gcccgagtta gtccccaggg ctggatttct ccccttgacc   2580
agctgggagt atcctatatc cacagccttt ctcagtatcg tcattctcaa gctctgatca   2640
gagcctctcc tgcgtctttc caggtggagg ttcattgtat aagcaaacat cccttaaaga   2700
aagcattgac cgcttcttca cagacatcac acacctccag aaacaaagtt ctaacagact   2760
tagaatgaaa tcaaacagaa taaaccttgc atcaagtgtg atactcacaa cttcagatca   2820
gggaaggaag tgagaagtaa agaagtattc atttcaagcc aataaaataa tctccaaggg   2880
cttggtcgaa ggctgaaacc taaaatcagt gggaggaaat gatttatttc tctttcacca   2940
aaacatgatc acattcatat catcattttc ttttcttccc agggctaaa gacatgtgga   3000
gagcttacca agacatgaaa gaagccaact acagggtgc agacaaatac ttccacgccc   3060
gtggaaacta tgacgctgcc cgaaggggac ctggggtgc ctgggctgct aaagtgatca   3120
ggtaccaggg tccctgggga tgcagggatg ggtgagcaga gcttggctgc ctaggacaac   3180
ctggaagggc naagccttgg agaactttcc tgtaggctgt gngccctcnt cctcttaccc   3240
```

-continued

```
accttcctgc tctgtgccca ctgtgaagtc tgaggggctg aagagcagag caacttggtg      3300
ggacaggcga ctctccaccc ttnctctatg ggtgctgttc acccagcaca gggctgaggt      3360
gggctgagcc tgaggagcct cagggttgta gcccctcttt cnttggctcc tctcagagtc      3420
attgatccct tggaaagagg agagatgggg agggtggggc tgtggctcat agtcctggat      3480
taatcccctc cgtgccctct tccttttccag taacgccaga gagactattc agggaatcac     3540
agaccctctg tttaagggta tgaccaggga ccaggtacgg gaggattcga aggccgacca      3600
gtttgccaac gaatggggcc ggagtggcaa agaccccaac cacttcagac ctgctggcct      3660
gcctgacaag tactgagctg cctctctctc tgctcaggag atggggctgt gagtccccaa      3720
ggacagggac actgacctag agagttctct gtcctcagaa ggaagcagat ctaataaatg      3780
cttaagagat ggaatactga gactgtgtgt cattcttggt ataaggacag cctgttagtt      3840
ccaggactga tggccggaca ccgacgtgaa ggctgagcct gtgcctgtgt gtttggttct      3900
ggcacacaat ctcagcatca ttcaggacag acgccctctg cagccttccc taatcagacc      3960
cgccccctcc ccagacccct ctggtgacac gggggccatt tccaggccct tcactgtcag      4020
gccttctcac tccctgccgt tgtgtcctgt cccttctct gtcccaggt ctagtccct         4080
agcctgtcct ctgtgctctc tgtgtggggc atggacacag gaggactgga tggtggaatc      4140
ctgctccaga aactgccacc tggatctcct gttcatttct cagcagcacc tacaagtaca      4200
actatgagcc agtttctgtc tgtgcatccg gaactgcctc cagtgctgtt cccttccctc      4260
tcttttcctt gccttataca agttcccagg aacaaacatg tcaaggagtg gaggaataat      4320
ggcaacatga aaattcagag ccaggcgcct ttgtttgcct tggatatgat tcatgtcctc      4380
gagaggaagt cgttttcccc tcctggtcct ttctcaaccc agggaagcca gcagcagtta     4440
cttttttattg aggaaaacag tgtctcttat ggaagggagt tgggtctgtt agagcacagg     4500
aatttatgagt gactctgtga gtcataacaa tgctgaatat gtaaacgcat acatacacat     4560
aaataatgca catgaattat agagattatg ataaaataaa aattgataaa tgtatcagaa      4620
ccacaagcag aaattcataa tggaaaataa aagggtgtat catgaataaa gtcataatgg      4680
attcagtaat cttcatgttc catattccat ctgttgttgc tgttgttcag tcactcagtc      4740
atgttgactc ttagggaccc catgactgc agcatgccaa gtttccctgt ccttcactat       4800
cacttggagt ttgctcaaac tcatgtccat tgagtctgtg atgccattca accacctcat      4860
cctctgtggc ctccttgtcc tcctgccgtc agtctttccc agcgtaaggg tcttttccag      4920
tgagtcagct gtttgcagca gttggctaaa gaatggagct tcagcatcag tctttccaat      4980
caat                                                                   4984
```

<210> SEQ ID NO 32
<211> LENGTH: 131
<212> TYPE: PRT
<213> ORGANISM: Bos taurus

<400> SEQUENCE: 32

Met Asn Leu Ser Thr Gly Ile Ile Phe Cys Phe Leu Ile Leu Gly Val
1               5                   10                  15

Ser Ser Gln Arg Trp Gly Thr Phe Leu Lys Glu Ala Gly Gln Gly Ala
            20                  25                  30

Lys Asp Met Trp Arg Ala Tyr Gln Asp Met Lys Glu Ala Asn Tyr Arg
        35                  40                  45

Gly Ala Asp Lys Tyr Phe His Ala Arg Gly Asn Tyr Asp Ala Ala Arg
    50                  55                  60

```
Arg Gly Pro Gly Gly Ala Trp Ala Ala Lys Val Ile Ser Asn Ala Arg
65                  70                  75                  80

Glu Thr Ile Gln Gly Ile Thr Asp Pro Leu Phe Lys Gly Met Thr Arg
                85                  90                  95

Asp Gln Val Arg Glu Asp Ser Lys Ala Asp Gln Phe Ala Asn Glu Trp
            100                 105                 110

Gly Arg Ser Gly Lys Asp Pro Asn His Phe Arg Pro Ala Gly Leu Pro
            115                 120                 125

Asp Lys Tyr
    130

<210> SEQ ID NO 33
<211> LENGTH: 10
<212> TYPE: PRT
<213> ORGANISM: artificial sequence
<220> FEATURE:
<221> NAME/KEY: misc_feature
<223> OTHER INFORMATION: peptide of residues in C-terminal region of
      bovine SAA used as experimental control

<400> SEQUENCE: 33

Asp Ala Ala Gln Arg Gly Pro Gln Gln Ala
1               5                   10

<210> SEQ ID NO 34
<211> LENGTH: 4
<212> TYPE: PRT
<213> ORGANISM: synthetic
<220> FEATURE:
<221> NAME/KEY: misc_feature
<223> OTHER INFORMATION: conserved motif

<400> SEQUENCE: 34

Thr Phe Leu Lys
1
```

GENOMIC MAMMARY AMYLOID A SEQUENCE

CROSS-REFERENCE TO RELATED APPLICATIONS

This application is a continuation-in-part of the prior filed co-pending commonly owned international application designating the United States PCT/US00/29065 with an international filing date of Oct. 20, 2000 which was published under PCT Article 21 (2) in English which is a continuation of U.S. Provisional Application Nos. 60/218,482 filed Jul. 14, 2000 and 60/218,611 filed Jul. 17, 2000.

This application is also a continuation-in-part of commonly owned U.S. application Ser. No. 09/425,679, filed on Oct. 22, 1999, now U.S. Pat. No. 6,509,444.

FIELD OF THE INVENTION

The present invention relates to the field of immunology and mammalian immune systems. In particular, the invention provides novel isoforms of serum amyloid A, which are found in colostrum.

BACKGROUND OF THE INVENTION

Several scientific or patent publications are referenced in this patent application to describe the state of the art to which the invention pertains. Each of these publications is incorporated by reference herein, in its entirety.

Mammals respond to tissue injury, trauma or infection by executing a complex series of biological reactions in an effort to prevent further tissue damage, to initiate repair of damaged tissue, and to isolate and destroy infective organisms. This process is referred to as the inflammatory response, the early and intermediate stages of which are referred to as the acute phase response.

The acute phase response involves a wide variety of mediators, including cytokines, interleukins and tumor necrosis factor. It also involves a radical alteration in the biosynthetic profile of the liver. Under normal circumstances, the liver synthesizes a range of plasma proteins at steady state concentrations. Some of these proteins, the "acute phase" proteins are induced in the inflammatory response to a level many times greater than levels found under normal conditions. Acute phase proteins are reviewed by Steel & Whitehead (Immunology Today 15: 81–87, 1994).

One of the massively induced acute phase proteins is Serum Amyloid A (SAA). SAA actually comprises a family of polymorphic proteins encoded by many genes in a number of mammalian species. SAAs are small apolipoproteins that accumulate and associate rapidly with high-density lipoprotein 3 (HDL3) during the acute phase of the inflammatory response. Most SAA isoforms are induced in response to inflammation; however, certain SAAs (e.g., human SAA4) appear to be constitutively expressed or minimally induced in the inflammatory response.

The liver has been considered the primary site of SAA production. However, SAA production outside the liver has been found, on a limited basis. For instance, expression of SAA mRNA has been reported in human atherosclerotic lesions and in human cultured smooth muscle cells and monocyte/macrophage cell lines (Meek et al., 1994; Urieli-Shoval et al., 1994; Yamada et al., 1996), and a unique isoform of SAA (SAA3) is produced by rabbit synovial fibroblasts (Mitchell et al., J. Clin. Invest. 87: 1177–1185, 1991). More recently, it was discovered that SAA mRNA is widely expressed in many histologically normal epithelial tissues, including tissues of stomach, intestine, tonsil, breast, prostate, thyroid, lung, pancreas, kidney, skin and brain neurons (Urieli-Shoval et al., J. Histochem. Cytochem. 46: 1377–1384, 1998). The role of SAA in such tissues has not been elucidated, nor has it been determined if the SAAs present in those tissues are the same isoforms as those found in serum, or if they represent additional isoforms of SAA.

SUMMARY OF THE INVENTION

According to one aspect of the invention, a Serum Amyloid A (SAA) protein is provided, which is isolated and purified from mammalian colostrum and is produced by ductal epithelial cells of the mammary gland. In one embodiment, the SAA is isolated and purified from horse colostrum. Preferably, the horse colostrum SAA comprises (SEQ ID NO:3) or (SEQ ID NO:4) and one or more of a sequence selected from the group consisting of (SEQ ID NO:5), (SEQ ID NO:6), (SEQ ID NO:7) and (SEQ ID NO:8) See FIG. 1.

In another embodiment, the SAA is isolated and purified from cow colostrum, and preferably comprises an N-terminal amino acid sequence which is (SEQ ID NO:1).

Alternatively, the SAA is isolated and purified from sheep colostrum and preferably comprises an N-terminal amino acid sequence which is (SEQ ID NO:2). Further, an amino acid region from the N-terminal sequence of colostrum SAA has been shown to be preserved among most species and contains the active portion of the molecule for several of the important properties of the molecule.

According to another aspect of the invention, an isolated nucleic acid molecule that encodes a mammalian colostrum SAA is provided. The nucleic acid molecule may be a gene, cDNA or RNA and may be single-stranded or double stranded. In a preferred embodiment, the nucleic acid molecule comprises a sequence that encodes one or more of (SEQ ID NO: 1–8), or their conservatively modified variants. In a most preferred embodiment the nucleic acid molecule comprises (SEQ ID NO:12) See FIG. 2 or its conservatively modified variants, including other colostrum SAA sequences, a similarly identified sequence, or any other nucleic acid sequence which encodes a colostrum associated SAA as described in the teachings herein.

Further according to the invention the genomic sequence for mammalian bovine colostrum associated SAA has been determined including the intron regions and the flanking region. SEQ ID NO:31. Thus the invention also includes a nucleotide sequence which encodes colostrum associated SAA which includes one or more of the native noncoding or intron regions or their conservatively modified variants. According to another aspect of the invention, a population of synthetic oligonucleotides is provided, which includes sequences obtained by back-translating one or more of amino acid SEQ ID NOS: 1–8. One or more members of this population of oligonucleotides specifically hybridizes to a gene or cDNA that encodes a colostrum SAA.

According to another aspect of the invention, antibodies immunologically specific for one or more epitopes of colostrum SAA are provided. Preferably, the antibodies are immunologically specific for at least one epitope of the colostrum SAA that distinguishes colostrum SAA from serum SAA.

According to another aspect of the invention, a process is provided for obtaining SAA from a mammal. The process comprises the steps of: (1) providing a sample of colostrum from the mammal, and (2) separating SAA contained in the sample from other materials contained in the sample, thereby obtaining the SAA from the mammal. SAA produced by this process is also provided.

According to the invention the novel colostrum associated SAA particularly the highly conserved region, (TFLK) also has an ability to stimulate mucin 3 (MUC3) production. Thus colostrum associated SAA may be used to treat and prevent enteric infections or other mucin inhibited disease states, such as traveler's diarrhea, infant diarrhea, necrotizing enterocolitis, urinary infections, and provide veterinary medicine for prevention of diarrhea in herd animals. The invention thus includes pharmaceutical compositions comprising a pharmaceutically effective amount of colostrum associated SAA peptide and a carrier to treat these and other diseases with similar pathology. Finally, other epithelial cell linings of mucosal surfaces such as nasopharynx, bladder etc., which produce mucins may also be treated with the pharmaceutical compositions of the invention to stimulate mucin production to prevent or treat infections associated therewith.

In yet another embodiment, the specificity of the promoter can be used to stimulate SAA production to aid in treatment of diseases associated with the teats or other mammary tissue of animals. For example, the colostrum associated SAA promoter is induced by prolactin. Thus one could administer prolactin or other colostrum SAA inducing agent to stimulate its production and cause increased MAA at the mammary tissue of said animal. Other features and advantages of the present invention will be better understood by reference to the drawings, detailed descriptions and examples that follow.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1. N-terminal amino acid sequence alignment of tryptic fragments of cow (SEQ ID NO:1), sheep (SEQ ID NO:2) and horse (SEQ ID NO:3) colostrum SAA, tryptic digest fragments of horse colostrum SAA (SEQ ID NOS: 4–8), rabbit synovial fibroblast SAA3 (SEQ ID NO:9); horse serum SAA, (SEQ ID NO:10); and mink serum SAA1, (SEQ ID NO:11).

FIG. 2. Nucleotide and complete deduced amino acid sequences of bovine colostrum associated SAA cDNA. The nucleotide position is indicated on the right. The predicted amino acid sequence is shown in single-letter code above the coding sequence, the stop codon is indicated with an asterisk, and the presumed signal peptide cleavage site to remove the leader sequence is denoted by an inverted triangle. Sequences determined by Edman degradation of the purified colostrum associated SAA protein are double underlined. Residues back-translated for the initial degenerate oligonucleotide primers used in the PCR amplification of the colostrum associated SAA 300 bp cDNA sequence are italicized. Oligonucleotide primers M5GW2 and M3GW2 used in the PCR amplification of the 5' and 3' regions of the colostrum associated SAA cDNA sequence, respectively, are underlined.

FIG. 3. This graph shows the production of colostrum-SAA by the MAC-T bovine epithelial cells over a period of eight days after they were stimulated with prolactin. Measurable quantities of colostrum-SAA could be detected by day two.

FIG. 5. The listing of the amino acids as determined by sequence analysis. The major sequence contains the N-terminal sequence for colostrum-SAA.

FIG. 7 depicts the results of an assay measuring MUC3 specific mRNA from HT29GAL cells. It shows that the N-Terminal 10 amino acid, bovine Colostrum-SAA peptide containing TFLK stimulated the production of MiUC3 mRNA up to 1½ times that of base line control levels (significance of P<0.0002). The ideal concentration was 50 μg/ml medium.

FIG. 8 is a graph showing a comparison of MUC3 stimulating activity of the N-terminal 10 amino acid bovine colostrum-SAA peptide was compared activity of the "Limited Scramble", the "Total Scramble" and "C-Terminal peptides" on cells. FIG. 8 shows that the original N-Terminal peptide was the only peptide that stimulated MUC3 mRNA statistically significantly over the control values (P<0.008).

FIG. 9 is a graph of MUC2 production by HT29 cells under culture conditions favoring MUC2 expression. None of the peptides stimulated the production of MUC2 mRNA including the N-Terminal 10 amino acid peptide that stimulated MUC3 production. None of the experimental values were significantly different from control values.

FIG. 10. FIG. 10 is the genomic bovine colostrum associated SAA sequence comprising the introns, and flanking region of the gene. (SEQ ID NO: 13). The TATA box is double underlined in the promoter region for bovine mammary-associated serum amyloid A 3 (M-SAA3, MAA). The additional three upstream nucleotides (single underlined) from the TATA box are also conserved in most "milk protein" TATA boxes. The transcriptional start site is underlined and indicated above the nucleotide with +1. The beginning and ending of the three introns are denoted with an arrow above these regions. The start and stop codons are underlined and indicated above the nucleotides. The encoded amino acids are denoted under the double-stranded DNA sequence. The presumed signal peptide cleavage site to remove the leader sequence predicted by the SignalP program (Version 1.1) (Nielsen et al., 1997) with 100% certainty is denoted by an inverted triangle. The polyadenylation signal (3773 to 3778) is underlined and the probable site for cleavage and polyadenylation is indicated with a double arrow.

DETAILED DESCRIPTION OF THE INVENTION

I. Definitions

Figure 4A:
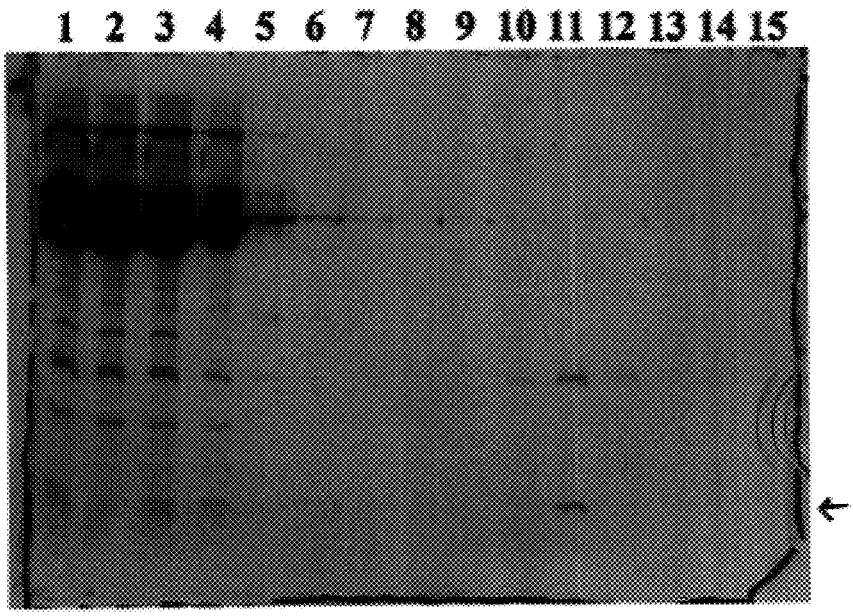
FIG. 4. SDS-PAGE 12% gel of the different fractions generated in the affinity purification of colostrum-SAA. The fractions are as follows: original culture fluid (lane 1), non-bound (lane 2), wash fractions (lanes 3–8) and eluted fractions (lanes 9–15). Blot (A.) is stained with CCB and (B.) the identical blot stained with a biotinylated anti-SAA monoclonal antibody. Lane 11 contains the colostrum-SAA as identified with the monoclonal antibody. This is the fraction that was used for amino acid sequence analysis and for IEF.

Various terms relating to the compositions and methods of the present invention are used herein above and also throughout the specification and claims.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "colostrum associated serum amyloid"A, "mammary amyloid A", "colostrum associated SAA" and/or "colostrum SAA" are used interchangeably and include but are not limited to the sequences disclosed herein, their conservatively modified variants, regardless of source and any other variants which retain the biological properties of the colostrum SAA and as demonstrated by the assays disclosed herein.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

With respect to proteins or peptides, the term "isolated protein (or peptide)" or "isolated and purified protein (or peptide)" is sometimes used herein. This term may refer to a protein that has been sufficiently separated from other proteins with which it would naturally be associated, so as to exist in "substantially pure" form. Alternatively, this term may refer to a protein produced by expression of an isolated nucleic acid molecule.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

Unless otherwise stated, the term "colostrum associated SAA encoding nucleic acid" is a nucleic acid of the present invention and means a nucleic acid comprising a polynucleotide of the present invention encoding a colostrum associated SAA. A "colostrum associated SAA gene" is a gene of the present invention and refers to a heterologous genomic form of a full-length colostrum associated SAA polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2$^{nd}$ ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, phosphorylation, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention. With respect to a protein, the term "N-terminal region" shall include approximately 50 amino acids adjacent to the amino terminal end of a protein.

As used herein "TFLK motif" shall include any formulation whether by amino acids or otherwise that would maintain the structural integrity and biological activity of the TFLK active site of colostrum SAA.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and may be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m=81.5°$ C.$+16.6(\log M)+0.41(\%GC)-0.61(\%form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995).

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

Nucleic acid sequences and amino acid sequences can be compared using computer programs that align the similar sequences of the nucleic or amino acids thus define the differences. The BLAST programs (NCBI) and parameters used therein are used by many practitioners to align amino acid sequence fragments. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by Best-Fit program may also be used to compare sequence identity and similarity.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art i.e., conditions of stringency (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In procaryotes, yeast, and mammalian cells for example, the transforming DNA may be maintained on an episomal element such as a plasmid. With respect to eucaryotic cells, a stably transformed cell is one in which the transforming DNA has become integrated into a chromosome so that it is inherited by daughter cells through chromosome replication. This stability is demonstrated by the ability of the eucaryotic cell to establish cell lines or clones comprised of a population of daughter cells containing the transforming DNA.

A "clone" is a population of cells derived from a single cell or common ancestor by mitosis. A "cell line" is a clone of a primary cell that is capable of stable growth in vitro for many generations.

II. Description

Serum amyloid A (SAA) is an acute phase protein which is produced in the liver and occurs at elevated levels in the serum of mammals as part of the inflammatory response related to tissue injury or infection. The inventors have discovered a unique isoform of SAA that occurs at highly elevated levels in colostrum. Elevated colostrum SAA in healthy cows returns to background levels found in milk within four days after calving. Colostrum SAA is believed to be produced locally (i.e., by mammary ductal epithelial cells), in colostrum and occurs independently of the blood concentration of acute phase SAA (A-SAA) (in samples of colostrum, whey and serum taken from five test cows, serum SAA was found to be in the range of 15 µg/ml, while in colostrum, SAA was elevated to levels in the average range of 300 µg/ml).

The unique isoform of SAA in colostrum may be fulfilling a variety of functions relating to the general role of colostrum in the development of neonatal immunity. For instance, colostrum SAA may act as vehicle for transport of lipids and immunoglobulins across the endothelial membranes of gut and/or vasculature in the newborn. It may be produced locally by the vascular endothelium after injury, and serve as a vehicle for transport of immunoglobulins into the intravascular space. In general, colostrum SAA is likely to have anti-microbial activity (either directly or indirectly) and to regulate the immune response in some manner. Colostrum SAA also may be involved in tissue remodeling by inducing enzymes involved in tissue repair and degradation, and by regulating production of protective mucins in mucosal tissue.

An elevated level of SAA has been detected in the colostrum of cows, horses, sheep and pigs. It has been purified from cow, sheep and horse colostrum, using methods such as those described in Example 3. Purified colostrum SAA from these sources was subjected to N-terminal amino acid sequence analysis. These sequences are set forth below, compared with the corresponding sequence of SAA3 from rabbit synovial fibroblasts.

Colostrum:
Cow(SEQ ID NO:1): MWX<u>TFLKEAGQGAKDMWRAY</u>
Sheep (SEQ ID NO:2): WLL<u>TFLKEAG</u>
Horse (SEQ ID NO:4): RELK<u>TFLKEAGQG</u>

Synovial fibroblasts:
Rabbit SAA3
(part of SEQ ID NO:9): REWL<u>TFLKEAGQGAKDMWRAY</u>SDMKEA The colostrum-derived SAAs share a unique amino acid sequence TFLK (TFLK motif) in the amino-terminal (or N-terminal) end. The TFLK motif is not found in any of the serum-derived SAAs from any mammal, but does share homology with SAA3 produced by rabbit synovial fibroblasts. The human SAA3 pseudogene (not expressed in serum or tissue) also comprises a deduced amino acid sequence that contains the TFLK sequence motif.

Further analysis of tryptic digest fragments of horse colostrum SAA revealed, however, that colostrum SAA is indeed a unique SAA. Sequences of the tryptic fragments of horse colostrum SAA are set forth below (SEQ ID NO: 4 is an alternate of SEQ ID NO:3).
(SEQ ID NO:3) REWFTFL
(SEQ ID NO:5) EANYIGADKYFH
(SEQ ID NO:6) GNYDAAQRGPGGA
(SEQ ID NO:7) VTDLFK
(SEQ ID NO:8) SGKDPNHFRPHGLPDKY In FIG. 1, the five horse colostrum SAA tryptic fragment sequences(SEQ ID NOS: 3–8) and the N-terminal sequences from cow and sheep and horse colostrum SAA (SEQ ID NOS: 1–3) are shown in alignment with the complete amino acid sequences of synovial fibroblast SAA3 from rabbit (SEQ ID NO:9), horse serum SAA (SEQ ID NO:10) and serum SAA1 from mink (SEQ ID NO:11). As can be seen from the alignment, horse colostrum SAA shares regions of similarity with each of rabbit synovial fibroblast SAA3, horse serum SAA and mink serum SAA1, yet is distinct from each of these proteins.

Thus, the present invention provides a novel SAA isoform isolated from colostrum. Although the horse, cow and sheep colostrum SAAs are exemplified herein, the present invention includes the colostrum SAA isoform from any mammalian species, inasmuch as the present inventors have identified colostrum SAAs from several mammalian species. Furthermore, as described in greater detail below, nucleic acid molecules encoding colostrum SAAs are also contemplated as being part of the present invention, as are antibodies immunologically specific for this novel SAA isoform.

According to the invention the cDNA of bovine colostrum associated SAA has been determined making possible the production of recombinant forms of the protein by methods known in the art and disclosed herein. (SEQ ID NO:12) See FIG. 2, is the cDNA sequence for the protein and the invention comprises this sequence as well as conservatively modified variants. Further disclosed is the active region of the protein which is highly conserved, as well as the properties of the protein which make it useful for assays to detect inflammation associated with mastitis or for pharmaceutical preparations for treating gastrointestinal disorders by stimulating mucin production.

Also according to the invention the genomic sequence of bovine colostrum associated SAA has been determined including the 3' and 5' untranslated regions as well as several intron regions. These non-coding genomic sequences are often required to obtain the highest expression of the coding regions when using an expression construct to obtain recombinant protein. Thus as disclosed herein the invention comprises a nucleotide sequence encoding bovine colostrum associated SAA that includes portions of non-coding sequences as disclosed herein. Preferably these non-coding regions comprise those adjacent to exons and more preferably comprise from about at least about 50 contiguous bases to maximize expression. Even more preferred the entire non-coding region or its conservatively modified variant may be used. These non-coding regions include bases 1–647, 739–2982, 3122–3510, 3674–4984 or their conservatively modified variants of SEQ ID NO:3 1.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al." are used.

A. Preparation of Colostrum SAA, Antibodies Specific for Colostrum SAA and Nucleic Acid Molecules Encoding Colostrum SAA 1. Proteins and Antibodies Colostrum SAA may be prepared in a variety of ways, according to a variety of methods that have been developed for purifying SAA from serum. One such method is set forth in Example 3. Variations in hydrophobic chromatography matrix systems and eluants also may be employed, such as those described by Smith et al. (Protein Expression & Purification 2: 158–161, 1991).

Alternatively, the availability of amino acid sequence information, such as (SEQ ID NOS: 1–8), enables the isolation of nucleic acid molecules encoding colostrum SAA. This may be accomplished using anti-colostrum SAA antibodies to screen a cDNA expression library from a selected species, according to methods well known in the art. Alternatively, a series of degenerate oligonucleotide probes encoding parts or all of (SEQ ID NOS: 1–8) FIG. 1 may be used to screen cDNA or genomic libraries, as described in greater detail below.

Once obtained, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. The pCITE in vitro translation system (Novagen) also may be utilized.

According to a preferred embodiment, larger quantities of the proteins may be produced by expression in a suitable procaryotic or eucaryotic system. For example, part or all of a colostrum SAA-encoding DNA molecule may be inserted into a vector adapted for expression in a bacterial cell (such as *E. coli*) or a yeast cell (such as *Saccharomyces cerevisiae*), or a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

Colostrum SAA produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The present invention also provides antibodies capable of binding to colostrum SAA from one or more selected species. Polyclonal or monoclonal antibodies directed toward part or all of a selected colostrum SAA may be prepared according to standard methods. Monoclonal antibodies may be prepared according to general methods of Köhler and Milstein, following standard protocols. In a preferred embodiment, antibodies are prepared, which react immunospecifically with selected epitopes of colostrum SAA that distinguish it from other SAAs.

2. Nucleic Acid Molecules

Once sequence information is obtained, nucleic acid molecules encoding colostrum SAA may be prepared by two general methods: (1) they may be synthesized from appropriate nucleotide triphosphates, or (2) they may be isolated from biological sources. Both methods utilize protocols well known in the art.

The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Nucleic acid molecules encoding colostrum SAA also may be isolated from mammalian species of interest using methods well known in the art. Nucleic acid molecules from a selected species may be isolated by screening cDNA or genomic libraries with oligonucleotides designed to match a nucleic acid sequence specific to a colostrum SAA-encoding gene. If the gene from a species is desired, the genomic library is screened. Alternatively, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al., *Molecular Cloning*, 1989, Cold Spring Harbor Press, Cold Spring Harbor N.Y.).

Alternatively, PCR (polymerase chain reaction) primers may be designed by the above method to encode a portion of colostrum SAA protein, and these primers used to amplify nucleic acids from isolated cDNA or genomic DNA. In a preferred embodiment, the oligonucleotides used to isolate colostrum SAA-encoding nucleic acids are designed to encode sequences unique to colostrum SAA, as opposed to serum SAA.

In accordance with the present invention, nucleic acids having the appropriate sequence homology with a colostrum SAA-encoding nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989, supra):

$$T_m = 81.5° C. + 16.6 \text{ Log}[Na+] + 0.41(\% G+C) - 0.63(\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. In a preferred embodiment, the hybridization is at 37° C. and the final wash is at 42° C., in a more preferred embodiment the hybridization is at 42° and the final wash is at 50°, and in a most preferred embodiment the hybridization is at 42° C. and final wash is at 65° C., with the above hybridization and wash solutions.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and wash in 0.1×SSC and 0.5% SDS at 65° C. for 15 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

Colostrum SAA-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence, of a nucleic acid molecule of the present invention. Such oligonucleotides are useful as probes for detecting colostrum SAA-encoding genes or mRNA in test samples, e.g. by PCR amplification.

B. Uses of Colostrum SAA Protein, Antibodies and Nucleic Acids

1. Proteins and Antibodies

Purified colostrum SAA, or fragments thereof, may be used to produce polyclonal or monoclonal antibodies which may serve as sensitive detection reagents for the presence and accumulation of the proteins in cultured cells or tissues and in intact organisms. Recombinant techniques enable expression of fusion proteins containing part or all of a selected colostrum SAA. The full length protein or fragments of the protein may be used to advantage to generate an array of monoclonal or polyclonal antibodies specific for various epitopes of the protein, thereby providing even greater sensitivity for detection of the protein. In a preferred embodiment, fragments of colostrum SAA that distinguish colostrum SAA from serum SAAs are utilized for generating epitope-specific antibodies.

Polyclonal or monoclonal antibodies immunologically specific for colostrum SAA may be used in a variety of assays designed to detect and quantitate the proteins. Such assays include, but are not limited to, (1) immunoprecipitation followed by protein quantification; (2) immunoblot analysis (e.g., dot blot, Western blot) (3) radioimmune assays, (4) nephelometry, turbidometric or immunochromatographic (lateral flow) assays, and (5) enzyme-coupled assays, including ELISA and a variety of qualitative rapid tests (e.g., dip-stick and similar tests).

Polyclonal or monoclonal antibodies that immunospecifically interact with colostrum SAA can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

2. Nucleic Acids

Colostrum SAA-encoding nucleic acids may be used for a variety of purposes in accordance with the present invention. The DNA, RNA, or fragments thereof may be used as probes to detect the presence of and/or expression of the genes. Methods in which colostrum SAA-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR) and reverse transcriptase-PCR (RT-PCR).

The exemplified colostrum SAA-encoding nucleic acids of the invention (e.g., cow, sheep, horse) may also be utilized as probes to identify related genes from other species, including humans. As is well known in the art and described above, hybridization stringencies may be adjusted to allow hybridization of nucleic acid probes with complementary sequences of varying degrees of homology.

In addition to the aforementioned uses of colostrum SAA-encoding nucleic acids, they are expected to be of utility in the creation of transgenic cells, tissues and organisms.

The present invention provides novel purified and isolated nucleic acid sequences encoding bovine colostrum associated SAA protein. In presently preferred forms, the DNA sequences comprise cDNA sequences encoding the novel SAA, or its conservatively modified variants, which are present in colostrum, comprise the active TFLK region and which possess the biological activity of the proteins disclosed herein. In a more preferred embodiment the nucleic acid sequence comprises at least about 93% identity to (SEQ ID NO:12) or 92% identity of the encoded amino acid sequence. Specifically, the sequence isolated is depicted in (SEQ ID NO:12). Alternate DNA forms such as genomic DNA, and DNA prepared by partial or total chemical synthesis from nucleotides as well as DNA with deletions or mutations, is also within the contemplated scope of the invention.

Further according to the invention genomic bovine colostrum associated SAA sequences have been characterized and identified. The genomic region including introns can be used with the colostrum SAA sequences and are often necessary to achieve the most efficient expression of colostrum SAA.

Association of DNA sequences provided by the invention with homologous or heterologous species expression control DNA sequences such as promoters, operators, regulators, and the like, allows in vivo and in vitro transcription from mRNA which, in turn, is susceptible to translation to provide the novel sodium channel proteins of the invention, and related poly- and oligo-peptides in large quantities. In a presently preferred DNA expression system of the invention colostrum associated SAA encoding DNA is operatively linked to a regulatory promoter DNA sequence allowing for in vitro transcription and translation of the protein.

Incorporation of DNA sequences into prokaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources. Use of mammalian host cells is expected to provide for such post-translational modifications (e.g. truncation, glycosylation, and tyrosine, serine, or threonine phosphorylation) as may be needed to confer optimal biological activity on recombinant expression products of the invention as more fully set forth hereinafter.

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both prokaryotic and eucaryotic systems may be used to express colostrum associated SAA encoding sequences; prokaryotic hosts are, of course, the most convenient for cloning procedures. Prokaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used prokaryotic control sequences which are defined herein to include promoters for transcription initiation, optionally with an operator, along with ribosome binding site sequences, include such commonly used promoters as the beta-lactase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enx* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

Also according to the invention the promoter sequences herein may be used with other heterolgous genes the production of which is desired in a host cell or tissue. The colostrum SAA promoter can be used as an inducible promoters to cause the production of operably linked sequences in response to prolactin or can be used to facilitate temporal and spatial expression of linked gene sequences to the mammary tissue and excreted in milk of the transgenic animal. Any gene sequence capable of being expressed in a host cell may be operably linked to the promoter of the invention and used in this manner. For example bovine serum albumin could be operably linked to the colostrum SAA of the invention causing transgenic BSA to be produced in the milk of said animal.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMT1I (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci (USA)* 1972) 69:2110, or the rbCl2 method described in Maniatis, et al, *Molecular Cloning: A Laboratory Manual* (1982) Cold Spring Harbor Press, p. 254 and Hanahan, D., *J Mol Biol* (1983) 166: 557–580 maybe used for prokaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 maybe used. Transformations into yeast maybe carried out according to the method of Beggs, J. D. *Nature* (1978) 275:104–109 or of Hinnen, A., et al, *Proc Natl Acad Sci (USA)* (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and relegated in the form desired.

The DNA sequences which form the vectors are available from a number of sources. Backbone vectors and control systems are generally found on available "host" vectors which are used for the bulk of the sequences in construction. Typical sequences have been set forth above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire sequence for genes or cDNA's of sizable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7γ pmoles γ32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl2, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 μl volumes under the following standard conditions and temperatures: for example, 20 mM Tris-Cl pH 7.5, 10 mM MgCl$_2$, 10 mM DTT, 33 μg/ml BSA, 10 mM–50 mM NaCl, and either 40 μM ATP, 0.01–0.02 (Weiss) units T4 DNA ligase at 0 C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per μg of vector at 60° for about one hour. In order to recover the nucleic acid fragments, the preparation is extracted with phenol/chloroform and ethanol precipitated. Alternatively, re-ligation can be prevented in vectors which have been double digested by additional restriction enzyme digestion and/or separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al, *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

Correct ligations for plasmid construction can be confirmed by first transforming *E. coli* strain MC1061 obtained from Dr. M. Casadaban (Casadaban, M., et al, *J Mol Biol* (1980) 138:179–207) or other suitable host with the ligation mixture. Successful transformants are selected by ampicillin, tetracycline or other antibiotic resistance by using other markers depending on the mode of plasmid construction, as is understood in the art. Plasmids from the transformants are then prepared according to the method of Clewell, D. B., et al, *Proc Natl Acad Sci* (*USA*) (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem Acids Res* (1979) 7:1513-1523. The isolated DNA is analyzed by restriction and/or sequenced by the dideoxy nucleotide method of Sanger, F., et al, *Proc Natl Acad Sci* (*USA*) (1977) 74:5463 as further described by Messing, et al, *Nucleic Acids Res* (1981) 9:309, o4 by the method of Maxam, et al, *Methods in Enzymology* (1980) 65:499.

Hosts Exemplified

Host strains used in cloning and prokaryotic expression herein are as follows:

For cloning and sequencing, and for expression of construction under control of most bacterial promoters, *E. coli* strains such as MC1061, DH1, RR1, C600hfl, K803, HB101, JA221, and JM101 can be used.

3. Assays Based on the Discovery of SAA in Colostrum

The discovery of a specific, constitutively expressed form of SAA in colostrum enables a new way of detecting the presence of colostrum in a sample containing a mixture of biological fluids (e.g., colostrum and milk). For instance, since SAA is elevated in colostrum and not in milk from normal mammary tissue, the measurement colostrum SAA in a milk sample can be used to differentiate colostrum from milk. Accordingly, in instances where it is undesirable to have milk that contains colostrum (some countries have laws to this effect), an immunological or hybridization assay, as described above, may be used to detect colostrum-tainted milk. Accordingly, in instances where it is undesirable to have milk that contains colostrum, an immunological or hybrization assay, as described above, may be used to detect colostrum tainted milk.

Colostrum SAA also may be used for a variety of other purposes. These include, but are not limited to its use as (1)

a carrier for delivery of molecules across the gut or vasculature, (2) a nutritional supplement for development of the gut mucosa in newborns, and (3) as a regulator of immune responses (via injection or oral administration).

4. Pharmaceutical Preparations

According to the invention Applicant has discovered that the colostrum associated SAA of the invention and more particularly its active site, (the TFLK motif) stimulate mucin production in the intestine. This is significant as mucins have been shown to have a key role in the prevention and treatment of intestinal infections and many probiotics act through inducing mucin production. See Mack et al, "Probiotics inhibit enteropathogenic *Escherechia coli* adherence in vitro by inducing intestinal mucin gene expression", 1999, Am J Physiol, 4 Part 1 G941–950, the disclosure of which is incorporated herein by reference. Thus the invention also includes pharmaceutical preparations for animals involving colostrum associated SAA. Those skilled in the medical arts will readily appreciate that the doses and schedules of pharmaceutical composition will vary depending on the age, health, sex, size and weight of the animal rather than administration, etc. These parameters can be determined for each system by well-established procedures and analysis e.g., in phase I, II and III clinical trials.

For administration, the colostrum associated SAA can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, drageemaking, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffinhydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in watersoluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers.

In addition to administration with conventional carriers, active ingredients may be administered by a variety of specialized delivery drug techniques which are known to those of skill in the art. The following examples are given for illustrative purposes only and are in no way intended to limit the invention.

As used herein the term "an effective amount" shall mean an amount of colostrum associated SAA sufficient to increase mucin production so that adherence of pathogens to mucosal cells is decreased as determined by the methods and protocols disclosed herein.

According to the invention, the novel colostrum associated SAA and more particularly its TFLK motif active site has been shown to stimulate mucin production, more specifically MUC3. Mucin production has been shown to inhibit the adherence of *E coli*, and probiotic agents which do the same, have been shown to work through stimulation of mucins. The colostrum associated SAA and/or peptide can be used as a probiotic.

The significance of mucins in intestinal infections lies in their ability to PREVENT the events necessary for infectious organisms to cause disease.

Mucins are produced by intestinal epithelial cells and secreted onto their surface. Thus, mucins are strategically located between the epithelial cells of the gut and offending agents ingested into the intestinal tract (i.e. infectious agents, noxious substances).

Mucins also inhibit the adherence of bacteria to the epithelial cells of the intestinal tract. Binding of bacteria to the lining cells of the gut is the first step in invasion, toxin delivery and development of diarrheal disease. If binding of the enteric pathogens is inhibited then disease does not develop.

Mucins have been shown to inhibit replication of viruses.

Mucins are part of innate immunity and a basic defense system of the gut. Thus, in comparison to the antibody/T-cell driven acquired immune system, mucins provide advantages including: immediate or rapidly inducible response to offending agents; broad spectrum of action; locally effective; intact across animal kingdom.

Increased production of mucins are possible by influences outside of the intestinal cell.

Increased mucin secretion due to infectious agents is a well-known clinical phenomenon. Mucin inhibits infectious intestinal bacteria from attaching to intestinal cells and thus, prevents infection. This is accomplished by mucins attaching to the structures on the wall of the bacteria that would normally be used to attach to the cells. Probiotic bacteria (non-infectious bacteria) prevent attachment of infectious intestinal bacteria to epithelial cells lining the intestinal tract. Secreted material from probiotic bacteria cause intestinal cells to produce more mucin and is the mechanism whereby probiotic agents prevent infection.

Applicant has demonstrated that colostrum associated SAA is present in the colostrum of mammalian species and is produced by ductal epithelial cells of the mammary gland. Further, by amino acid sequence analysis, that a portion of colostrum associated SAA is preserved among many animal species. Applicant has synthesized a 10 amino acid peptide from bovine colostrum associated SAA, which contains the TFLK motif, species-preserved region of the molecule. This peptide increases the production of MUC3 in cells isolated from the small intestine by activating the gene responsible for mucin production. Applicant has shown that the intestinal mucin genes are turned on very rapidly (within 30 minutes) by this peptide. Further, the increase in mucin production by this peptide is related to its concentration around the intestinal cells. Experiments show low concentrations of colostrum associated SAA peptide will not cause an increase in mucin production whereas too much colostrum associated SAA peptide will decrease the gene driven production of mucin. This phenomenon is very common in biological systems and shows that it is a specific dose dependent effect. A four amino acid region "TFLK" and the specific order of those four amino acids within the colostrum associated SAA peptide are responsible for stimulating mucin production. It has also been shown that other peptides of the amyloid molecule unrelated to the unique colostrum associated SAA region do not stimulate mucin production.

This demonstrates pharmaceutical applications of this peptide for numerous enteric pathologies. For example the prevention of traveler's diarrhea. Many infectious organisms are geographical in nature and travelers outside of their own areas have usually not been previously exposed to these organisms, thus have not developed immunity to them. Many people will take antibiotics before traveling, but some antibiotics have deleterious side effects and also organisms are becoming resistant to many antibiotics.

Another other potential use would be to prevent dysentery and other infectious diseases particularly for the military. Vaccine development is proving to be problematic. For example, failure of military recruits to take vaccination (anthrax vaccine) and disease caused by vaccinations leading to the removal from the market of the vaccine (rotavirus vaccine). Colostrum associated SAA is to be a rapid, safe and effective means to reduce or prevent intestinal-related infections.

Another example includes prevention or treatment of infant diarrhea. Breast fed infants have far fewer infections than formula fed infants. Since colostrum is a natural substance which is beneficial to the infant and colostrum associated SAA is a component of colostrum, it will be an invaluable natural addition to formula. Such formulas are commonly commercially available such as Infamel™, Similac™, Carnation Good Start™, and Gerber™. Probiotics have been shown to reduce severity and shorten the recovery time for viral caused diarrhea. Thus, another use for colostrum associated SAA would be for children with this condition which would also have an economic impact by reducing hospital stays and costs.

Yet another example includes the prevention or treatment of necrotizing enterocolitis (NEC). This is a serious complication that occurs in premature infants. With the various reproduction techniques that are being used there has been an explosion in the number of premature infants. Therapy for NEC has remained the same for the last few decades. Since bacteria in the gut of the premature infant have a major role in the development of NEC, therapy for this condition consists of keeping the infant from feeding, giving strong antibiotics and hoping that the bowel does not perforate.

Another example includes the prevention of diarrhea in areas of outbreaks. $E.\ coli$ 0157:H7 outbreaks causing which can lead to deaths from hemolytic-uremic syndrome. We have shown that mucin production prevents $E.\ coli$ from adhering to epithelial cells and thus could prevent this infection.

Yet another example includes the treatment or prevention of urinary tract infections. The bladder epithelial cells are very similar to intestinal epithelial cells and are capable of producing mucins. Therefore prevention of urinary infections, including hospitalized patients with urinary catheters, would also be a use for the pharmaceutical compositions of the invention.

Yet another example includes veterinary medicine, for the prevention of infectious diarrhea in herd animals to allow for removal of antibiotics from the feed.

Although this disclosure includes upregulation of intestinal mucins, epithelial cells lining other mucosal surfaces, (e.g. nasopharynx, bladder, etc.), also produce mucins. These mucins function to prevent infections analogous to intestinal mucins, and would also be effective targets for treatment according to the invention.

The following examples are provided to describe the invention in greater detail. They are intended to illustrate, not to limit, the invention.

EXAMPLE 1

Comparative Analysis of SAA in Serum, Colostrum and Whey

The purpose of this study was to determine if SAA levels in colostrum and whey corresponded to serum SAA levels in mastitis symptomless and symptomatic cows.

Colostrum, whey and serum samples were obtained from a challenge model study in which cattle were vaccinated against a gram positive organism. Two sets of samples were utilized: one set (4 cows) from vaccinated animals that displayed clinical symptoms of mastitis, and the other set (5 cows) from vaccinated animals showing no clinical symptoms. Sample designations are shown below:

| Vaccinates - Non Clinical (NC) | Vaccinates - Clinical (C) |
|---|---|
| NC Cow A | C Cow A |
| NC Cow B | C Cow B |
| NC Cow C | C Cow C |
| NC Cow D | C Cow D |
| NC Cow E | |

Whey/colostrum samples were obtained from the quarter displaying the clinical symptoms.

ELISA assays were conducted according to standard protocols, e.g., as described by McDonald et al. (J. Immunol. Meth. 144: 149–155, 1991), using rat anti-SAA (human) monoclonal antibodies that cross react with bovine SAA isoforms.

Results are shown in Table 1:

TABLE 1

Comparison of Bovine Mastitis Sera, Whey and Colostrum SAA values

| Nonclinical Samples: | | | Clinical Samples: | | |
|---|---|---|---|---|---|
| Sample | Sera ug/ml | Whey/ Colost. ug/ml | Sample | Sera ug/ml | Whey/ Colost. ug/ml |
| NCA Day 0 | 3.9 | 2.3 | CA Day 0 | 1.3 | 0.8 |
| NCA Day 14 | 1.4 | | CA Day 14 | 1.9 | |
| NCA Day 28 | 1.0 | | CA Day 28 | 1.1 | |
| NCA Day 42 | 1.1 | | CA Day 42 | 0.8 | |
| NCA calving | 13.6 | 117.8 | CA Calving | 3.6 | 1108.0 |
| NCA-C + 14 | 73.0 | 56.5 | CA C + 14 | 12.3 | 0.8 |
| NCA-C + 28 | 11.8 | 3.4 | CA C + 28 | 152.6 | 55.0 |
| NCB Day 0 | 2.6 | 2.3 | CB Day 0 | 2.7 | 1.8 |
| NCB Day 14 | 1.4 | | CB Day 14 | 21.4 | |
| NCB Day 28 | 1.2 | | CB Day 28 | 3.1 | |
| NCB Day 42 | 0.8 | | CB Day 42 | 1.0 | |
| NCB calving | 4.6 | 346.2 | CB Calving | 17.2 | 291.0 |
| NCB-C + 14 | 1.2 | 4.0 | CB C + 14 | 26.7 | 1.7 |
| NCB-C + 28 | 0.8 | 7.3 | CB C + 28 | 7.2 | 3.7 |
| NCC Day 0 | 3.1 | 1.8 | CC Day 0 | 1.9 | 1.9 |
| NCC Day 14 | 1.8 | | CC Day 14 | 2.0 | |
| NCC Day 28 | 1.4 | | CC Day 28 | 2.0 | |
| NCC Day 42 | 0.9 | | CC Day 42 | 0.9 | |
| NCC Calving | 24.5 | 15.8 | CC Calving | 18.0 | 5.8 |
| NCC C + 14 | 6.9 | 1.4 | CC C + 14 | 167.9 | 30.0 |
| NCC C + 28 | 6.8 | 9.1 | CC C + 28 | 1.3 | 8.4 |
| NCD Day 0 | 3.2 | 1.7 | CD Day 0 | 2.7 | 3.4 |
| NCD Day 14 | 0.9 | | CD Day 14 | 1.6 | |
| NCD Day 28 | 2.4 | | CD Day 28 | 1.8 | |
| NCD Day 42 | 0.8 | | CD Day 42 | 1.6 | |
| NCD Calving | 13.8 | 484.4 | CD Calving | 14.6 | 77.5 |
| NCD C + 14 | 1.3 | 1.6 | CD C + 14 | 1629.0 | 999.5 |
| NCD C + 28 | 1.2 | 5.0 | CD C + 28 | 33.1 | 2.5 |
| NCE Day 0 | 2.6 | 8.0 | | | |
| NCE Day 14 | 1.6 | | | | |
| NCE Day 28 | 1.9 | | | | |
| NCE Day 42 | 1.0 | | | | |
| NCE Calving | 33.2 | 89.1 | | | |
| NCE C + 14 | 7.8 | 0.6 | | | |
| NCE C + 28 | 5.5 | 4.3 | | | |

As can be seen from the results set forth in Table 1, SAA was present in high levels in the colostrum of cows at calving in 80% of the animals tested. SAA was not detected in whey samples of most clinically healthy cows fourteen days later. SAA levels in colostrum and whey were independent of the serum concentrations of SAA. Serum levels of SAA at calving of control cows were normal (15 µg/ml), whereas the average level in the colostrum at calving was about 300 µg/ml. In one cow, the colostrum SAA was as high as 1100 µg/ml. The mastitis challenged vaccinated cow CC displayed highly elevated serum levels of SAA, but SAA levels in the whey samples were almost normal. The vaccinated challenged cow CD displayed high levels of SAA in serum and in whey.

EXAMPLE 2

Evaluation of SAA in Colostrum and Subsequent Serial Samplings of Milk

The purpose of this study was to evaluate colostrum and subsequent serial milk samplings to determine SAA content. Samples were obtained from Holstein dairy cows at the University of Nebraska—Lincoln Dairy Research Facility. Samples of colostrum were taken at calving, and subsequent milk samples were taken twice weekly for three weeks. Samples from all four udder quadrants were pooled. Results are shown in Table 2.

TABLE 2

SAA Levels in Colostrum and Milk Samples

| Cow ID | Sample Day | SAA ug/ml |
|---|---|---|
| 83 colostrum | Calving | 184.8 |
| 83 milk | +4 | 0.2 |
| 83 milk | +7 | 0.0 |
| 83 milk | +11 | 0.0 |
| 83 milk | +14 | 0.0 |
| 83 milk | +18 | 0.0 |
| 83 milk | +21 | 0.0 |
| 908 colostrum | Calving | 135.6 |
| 908 milk | +4 | 2.6 |
| 908 milk | +7 | 9.1 |
| 908 milk | +11 | 8.2 |
| 908 milk | +14 | 2.0 |
| 908 milk | +18 | 2.1 |
| 908 milk | +21 | 3.6 |
| 961 colostrum | Calving | 364.6 |
| 961 milk | +4 | 0.3 |
| 961 milk | +7 | 0.5 |
| 961 milk | +11 | 0.0 |
| 961 milk | +14 | 0.0 |
| 961 milk | +18 | 0.0 |
| 961 milk | +21 | 0.0 |

The results show that SAA is elevated in colostrum of normal animals but in very low levels or not detected in normal milk samples after colostrum has cleared.

EXAMPLE 3

Purification of SAA from Colostrum

The procedure set forth below can be used for purification of SAA from serum, plasma, milk or colostrum from any animal species. The procedure comprises two basic steps: the SAA is purified to approximately 20% purity by hydrophobic chromatography, then further purified to approximately 95% purity by SDS-PAGE and electro-blotting.

Approximately 30 ml of octyl sepharose CL-4B (Pharmacia #17-0790-01) was prepared by washing it with approximately 10 volumes (300 ml) water to remove any traces of ethanol. This may be done by washing the gel in a sintered glass funnel (coarse, funnel volume 600 ml) or by adding the water to the gel in a beaker, and then allowing the gel to settle before pouring off the water and rewashing the gel.

The final washes (2×40 ml) of the gel were with a solution of 0.5M ammonium sulfate.

Prior to use, the colostrum was allowed to set at 4° C. to allow the lipid layer to separate from the aqueous layer, since the lipid portion seemed to interfere with the purification procedure. After the ammonium sulfate was poured off, 20 ml of the 4° C. refrigerated colostrum with elevated levels of SAA (preferably >1 μg/ml) was added to the gel (in the beaker). The suspension of colostrum and gel was swirled several times during the one hour incubation at room temperature so to allow the SAA to bind to the gel.

The gel was then poured into a 600 ml sintered glass funnel (coarse) and the non-bound fraction was collected. This non-bound fraction may be tested for SAA to determine the efficiency of binding.

The gel was washed with 5-times 50 ml 50 mM Tris, 10 mM NaCl buffer pH 7.6. The final wash should be clear.

The column was further washed with 2×50 ml of 30% isopropanol in Tris/NaCl. These washes were most thorough when a syringe with a 10 gauge needle was used to eject the isopropanol/buffer solution onto the gel. The gel was thoroughly mixed when this procedure was followed.

The SAA was eluted from the gel with a solution of 60% isopropanol in TRIS/NaCl. Generally this was done in four elutions of 10 ml each.

The eluates contained a variety of proteins, of which about 20% was SAA. In samples where the SAA was too dilute it was concentrated by evaporating the isopropanol in a centrifugal concentrator. (RC 1010, Jouan Inc.)

For further purification for sequencing or amino acid analysis the proteins in the eluates were separated by SDS-PAGE and transferred to PVDF membrane by electroblotting.

The band which was identified as SAA by SAA specific antibodies was then excised and used for sequencing.

EXAMPLE 4

Isolation of Colostrum Associated SAA cDNA

RNA Isolation: Total RNA for reverse transcription-polymerase chain reaction (RT-PCR) was isolated from mammary gland epithelial cells using TRIZOL (Gibco BRL) according to manufacturers recommendations. The integrity of the RNA was checked by fractionation on a 1% (wt/vol) agarose gel and subsequent ethidium bromide staining.

First Strand cDNA Synthesis: First strand cDNA synthesis was performed using SuperScript II RNase H-Reverse Transcriptase (Gibco BRL) essentially as described by the manufacturer. Briefly, 5 μg of total RNA was mixed together with RNase-free sterile water and 20 μM of the cDNA1-T14 primer (5'-GTTGTCGACTGTAGTGGAGT$_{14}$-3') (SEQ ID NO:14) to obtain a final volume of 12 μL. The reaction mixture was incubated for 10 minutes at 75° C. and then incubated at room temperature for 10 minutes. The mixture was then placed on ice while 4 μL of 5× First Strand Buffer (Gibco BRL), 2 μL of 0.1 M DTT, and 1 μL of 10 mM dNTP mix (10 mM dATP, 10 mM dGTP, 10 mM dCTP, and 10 mM dTTP at neutral pH) was added. The contents of the reaction were gently mixed and incubated at 42° C. for 2 minutes. SuperScript II RNase H-Reverse Transcriptase (200 Units) was added to the reaction. Following gently mixing, the reaction was incubated at 42° C. for 1 hour. The reverse transcriptase was inactivated by heating the mixture to 70° C. for 15 minutes. To remove RNA complementary to the cDNA, 2 Units of *Escherichia coli* RNase H (Gibco BRL) was added and the mixture was incubated at 37° C. for 20 minutes. The reaction mixture was stored at −20° C. until needed for second strand cDNA synthesis.

Second Strand cDNA Synthesis and Polymerase Chain Reaction: Second strand cDNA synthesis and amplification of the double stranded cDNA was performed using either Platinum Taq DNA Polymerase High Fidelity (Gibco BRL) or AmpliTaq DNA Polymerase (PE Applied Biosystems), each according the manufacturer's recommendations for the respective DNA polymerase. The PCR reactions (50 μL) with Platinum Taq DNA Polymerse High Fidelity contained 5 μg of the cDNA previously described, 20 μM of the forward primer, 20 μM of the reverse primer, 5 μL 10× High Fidelity PCR Buffer (Gibco BRL), 1 μL 10 mM dNTP mix, 2 μL 50 mM magnesium sulfate, 1 Unit Platinum Taq DNA Polymerase High Fidelity (Gibco BRL), and sterile water to obtain a final volume of 50 μL. The thermal cycling parameters with Platinum Taq DNA Polymerase High Fidelity (Gibco BRL) were 40 cycles for 30 seconds at 94° C., 15–30 seconds at 45–56° C., and 1–4 minute at 50° C.

The PCR reactions (50 μL) with AmpliTaq DNA Polymerase (PE Applied Biosystems) contained 5 μg of the cDNA previously described, 20 μM of the forward primer, 20 μM of the reverse primer, 5 μL 10× GeneAmp Buffer containing 15 mM magnesium chloride (PE Applied Biosystems), 1 μL 10 mM dNTP mix, 1.3 Units AmpliTaq DNA Polymerase (PE Applied Biosystems), and sterile water to obtain a final volume of 50 μL. The thermal cycling parameters with AmpliTaq DNA Polymerase (PE Applied Biosystems) were initiated with a hot start followed by 40 cycles for 1 minute at 95° C., 30 seconds at 50° C., and 1 minute at 72° C., and then 1 cycle for 15 minutes at 72° C.

The initial oligonucleotide primers suitable for PCR amplification of colostrum associated SAA cDNA were designed by back-translating the amino acid sequence obtained from colostrum associated SAA amino-terminus and tryptic digested fragments (see FIG. 2). The forward degenerate primer F1C (5'-ACNTTYCTNAARGARGC-NGGNCA-3') (SEQ ID NO:15) and reverse degenerate primer R3B (5'-GAAGTGRTTGGGGTCTTTGCCACT-3') (SEQ ID NO:16), which correspond to amino-terminal residues TFLKEAGQ (SEQ ID NO:17) and carboxy-terminal residues SGKDPNHF (SEQ ID NO:18) in the mature colostrum associated SAA protein, respectively, were used in PCR for the initial amplification of the 300 bp middle cDNA sequence for colostrum associated SAA. The 5' cDNA sequence for colostrum associated SAA was obtained by PCR and subsequent DNA sequencing using the forward primer M5RT2 (5'-AGCACAGGCAGCTCAGCTTCAC-CAGGA-3') (SEQ ID NO:19) and the reverse primer M5GW2 (5'-GAAGTATTTGTCTGCACCCCTGTAGTTG-GCTTCTT-3') (SEQ ID NO:20). The M5RT2 primer was based on SAA cDNA sequences deposited in GenBank and the M5GW2 primer was based on the 300 bp colostrum associated SAA cDNA sequence previously described (see FIG. 2). The 3' cDNA sequence for colostrum associated SAA was obtained by PCR and subsequent DNA sequencing using the forward primer M3GW2 (5'-CTGTTTAAGGG-TATGACCAGGGACCAGGTACG-3') (SEQ ID NO:21) and the reverse primer CDNA1 (5'-GTTGTCGACTG-TAGTGGAG-3') (SEQ ID NO:22). The M3GW2 primer was also based on the previously described 300 bp colostrum associated SAA cDNA sequence (see FIG. 2) and the CDNA1 primer was identical to the first 19 nucleotides of the primer CDNA1-T14 used in first strand cDNA synthesis (see above for CDNA1-T14 sequence).

Cloning of colostrum associated SAA cDNA: The resulting 300 bp RT-PCR product obtained with AmpliTaq DNA Polymerase (PE Applied Biosystems) using the degenerate oligonucleotides F1C and R3B was agarose gel purified using Qiagen's QIAquick Gel Extraction Kit and cloned into Invitrogen's pCRII-TOPO vector, according to the manufacturer's recommendations. The TOPO cloning reaction was transformed into *E. coli* TOP10 and plated on Luria-Bertani containing 50 µg/mL kanamycin and X-Gal, as recommended by Invitrogen. Putative positive colonies were screened using the M13 Forward (−20) and M13 Reverse primer in PCR. Re-amplified inserts were fractionated in a 2% (wt/vol) agarose gel and visualized by ethidium bromide staining along with an appropriate DNA size marker.

DNA Sequencing and Computer Analysis of colostrum associated SAA cDNA: The cloned 300 bp colostrum associated SAA cDNA sequence was re-amplified with the M13 Forward (−20) and M13 Reverse primers in high-fidelity PCRs. The 5' and 3' region of the colostrum associated SAA cDNA sequence was reamplified in high-fidelity RT-PCRs using the M5RT2/M5GW2 and M3GW2/CDNA1 primer pairs, respectively. The resulting amplicons were purified using Qiagen's Qiaquick PCR Purification System and sequenced in both directions by the DNA sequencing facility at Iowa State University (Ames, Iowa) in an automated ABI 377 DNA sequencer. The SP6 and T7-2 primers were used in the sequencing of the cloned 300 bp colostrum associated SAA cDNA. The primers M5RT2 and M5GW2 were used for sequencing of the 5' region of colostrum associated SAA cDNA and the primers M3GW2 and CDNA1 were used for sequencing of the 3' region of colostrum associated SAA cDNA. The DNA sequence was analyzed using the Wisconsin Genetics Computer Group (GCG) Package Version 10.1 (Madison, Wis.) SeqEd, PileUp, and BLASTX programs. The amino-terminal signal peptide cleavage site was identified by using the SignalP (version 1.1) program (Nielsen et al., 1997).

RT-PCR Detection of colostrum associated SAA and not Acute Phase SAA mRNA Expression by Bovine Mammary Gland Epithelial Cells: As previously described in detail, a 300 bp RT-PCR product was obtained from bovine mammary gland epithelial cells using the primer CDNA1-T14 for first strand synthesis from the mRNA present and then subsequent usage of the primers F1C and R3B for second strand synthesis and amplification. The figures show the nucleotide sequence obtained for this 300 bp RT-PCR product. This nucleotide sequence correlated with the peptide sequencing data obtained from the colostrum-associated and bovine mammary gland-associated SAA isoform (see FIG. 2).

The forward degenerate primer F2 (5'-GACATGTGGMGAGCCTACTCYGACATG-3') (SEQ ID NO:23) and reverse degenerate primer R3B (previously described) were used in RT-PCR for amplification of A-SAA cDNA. The forward primer F2 corresponds to amino-terminal residues DMWRAYSDM (SEQ ID NO:24) in the acute phase SAA (A-SAA) protein (SWISS-PROT accession number P35541) and the reverse primer R3B corresponds to the carboxy-terminal residues SGKDPNHF (SEQ ID NO:25) in both the A-SAA protein and the colostrum associated SAA protein. Subsequent cloning and nucleotide sequencing of the resulting 267 bp cDNA sequences correlated with colostrum associated SAA cDNA, strongly suggesting that colostrum associated SAA and not A-SAA transcripts were present.

The restriction endonuclease XhoI site was found to be present in the cDNA sequence of bovine A-SAA (data not shown), but was not found in the cDNA sequence of bovine colostrum associated SAA. XhoI restriction endonuclease digestion of the 300 bp and 267 bp CDNA sequences previously described did not cleave either of these two RT-PCR products. This result additionally suggested that only colostrum associated SAA and not A-SAA mRNA was transcribed by bovine mammary gland epithelial cells.

To further verify that colostrum associated SAA and not A-SAA mRNA was expressed by the bovine mammary gland epithelial cells, the forward colostrum associated SAA-specific primer M3GW2 (previously described and shown in FIG. 2) and reverse CDNA1 primer (previously described) were again used in RT-PCR. In addition, the forward A-SAA-specific primer S3GW1 (5'-TAAGGGTAC-GACCAGTGGCCAGGGTCA-3') (SEQ ID NO:26), corresponding to residues FKGTTSGQGQ (SEQ ID NO:27) in mature A-SAA) and the reverse CDNA1 primer (previously described) were used in RT-PCR. However, no RT-PCR product was observed using the forward A-SAA-specific primer and reverse CDNA1 primer, further confirming no expression or the low abundance of A-SAA mRNA expression by bovine mammary gland epithelial cells.

EXAMPLE 5

Colostrum-SAA Production by Bovine MAC-T Mammary Epithelial Cells

Bovine MAC-T mammary gland epithelial cells were obtained from ATCC (CRL-10274) and cultured according to recommended conditions (Turner, J D and Huynh H. Immortalized bovine mammary epithelial cell line. U.S. Pat. No. 5,227,301 dated Jul. 13, 1993). MAC-T cells were cultured on Dulbecco's Modified Eagles Media (DMEM) supplemented with 10% Fetal Calf Serum (FCS), 5 µg/ml insulin, 1 µg/ml hydrocortisone and fungizone. Cells were incubated at 37° C. with 5% $CO_2$. For colostrum-SAA production the cells were seeded onto type I Collagen coated plates. After 14 hours of incubation, the cells were washed twice with Dulbecco's phosphate buffered saline (DPBS) and incubated in media (DMEM, 5 µg/ml insulin, 1 µg/ml hydrocortisone and 2.5% FCS) supplemented with prolactin from sheep pituitary gland (5 µg/ml) for the stimulation of colostrum-SAA production. Approximately one half of the media was replaced daily with fresh prolactin supplemented media. Standard ELISA for the quantitation of SAA (FIG. 3) was used to assay aliquots of the growth media collected on the different days for the presence of colostrum-SAA.

Cells were kept in culture for 41 days in media supplemented with prolactin. Levels of colostrum-SAA production reached a maximum of almost 3000 ng/ml.

Figure 4B:
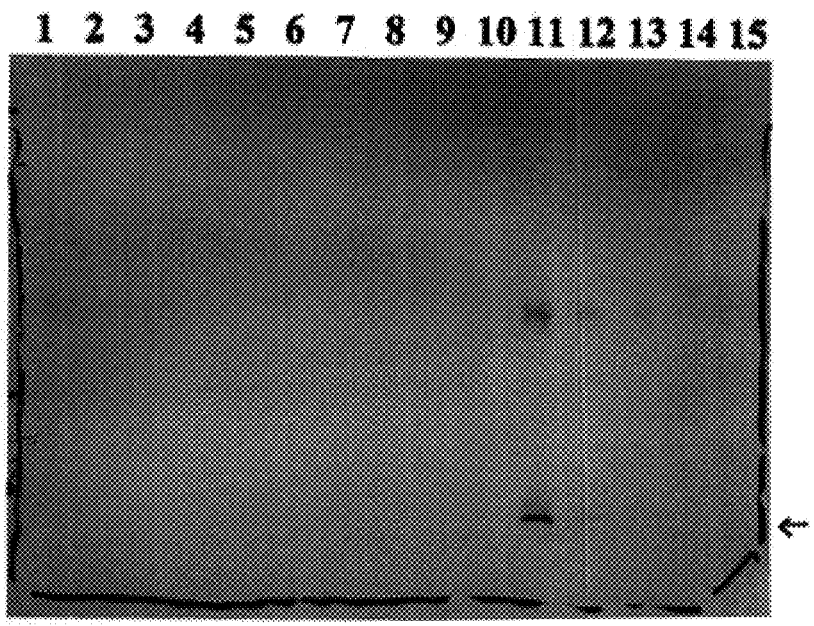
Figure 6A:
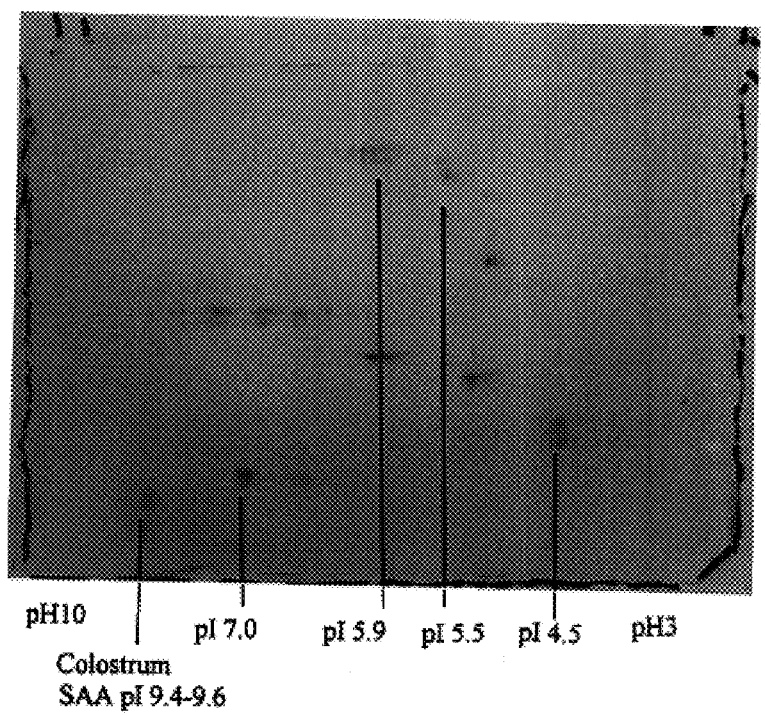
FIG. 6A. represents the blot of the 2-D gel which was obtained as a second dimension from the pH 3–10 IPG strip which was used for the isoelectric focusing of the affinity purified MAC-T cell fluid along with the standards. The blot has been stained with CBB so that all of the proteins are stained. The isoelectric point (pI) of some of the commercial standards as well as the approximate apparent pI of the colostrum SAA (pI range 9.4–9.6) have been noted on the figure. This agrees with the predicted pI of 9.6 for colostrum SAA using the compute pI/Mw tool of ExPASy Proteomic Server of the Swiss Institute of Bioinformatics.
Figure 6B:
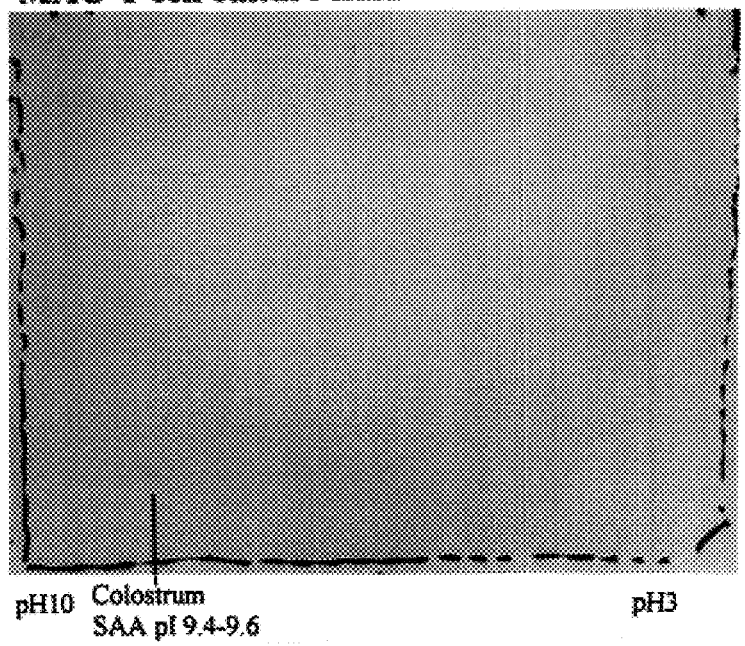
FIG. 6B. is the identical blot, but this has been stained with the monoclonal antibody with specificity to SAA. The only spot that stains is the one corresponding to the colostrum SAA and this spot matches the spot observed on the CBB stained blot.
Figure 6C:
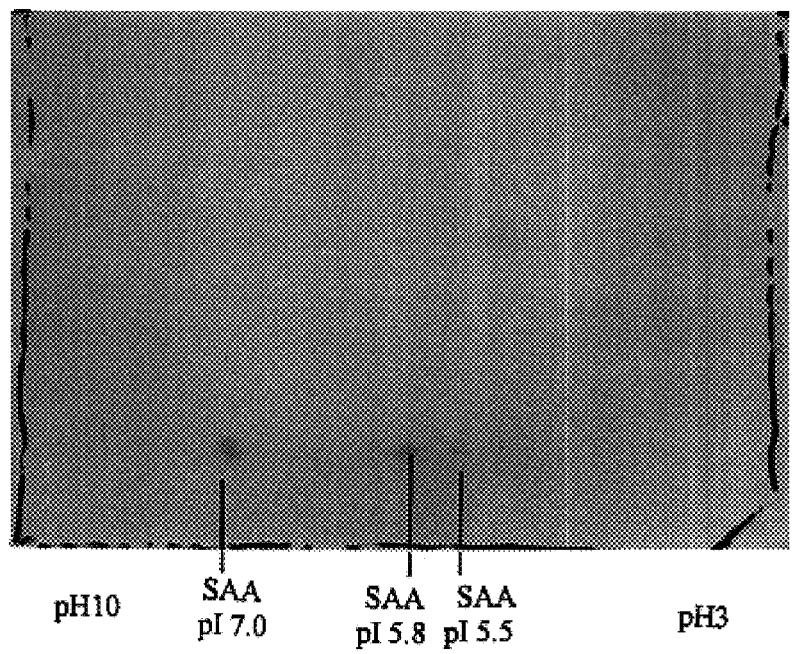
FIG. 6C. is the monoclonal antibody stained blot from the analysis of the semi-pure bovine serum. Three isoforms with the approximate apparent pI values of 7.0, 5.8 and 5.5 stain with the monoclonal antibody with specificity to SAA. FIG. D. is the monoclonal antibody stained blot of the 2-D gel from affinity purified bovine colostrum. Only the spot that corresponds to colostrum-SAA at the approximate apparent pI in the range of 9.4–9.6 stains with the monoclonal antibody. MAC-T generated SAA has pI of 9.4–9.6. Thus both the MAC-T culture fluid and the colostrum contain colostrum-SAA since the spots identified with the monoclonal antibody have the identical pI and molecular weight (12 Kda) and this value is significantly different from the pI of any of the isoforms found in the serum.
Figure 6D:
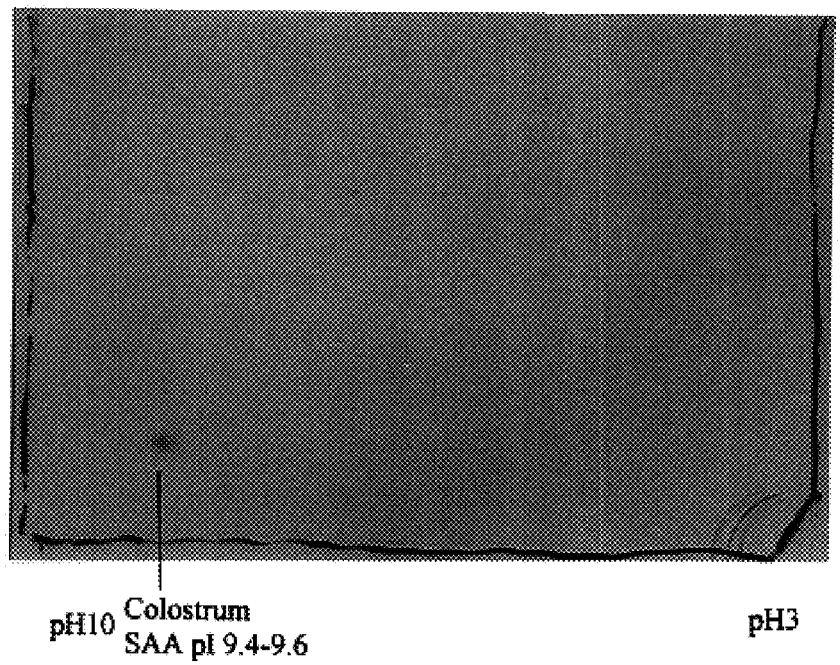
FIG. 6. These blots represent 2-D gels from the isoelectric focusing of MAC-T cell fluid (A. and B.), bovine serum (C.) and bovine colostrum (D.).

Purification of colostrum associated SAA from cell culture fluid. Colostrum-SAA was purified from cell culture fluid by affinity chromatography. Briefly, an affinity column was prepared by coupling a monoclonal antibody with specificity to SAA to cyanogen bromide activated sepharose 4B. Treating the column with 50 mM Tris, 0.1 NaCl, 0.2 M glycine pH 8 buffer blocked residual active groups on the gel. The column was then washed with 50 mM Tris, 0.1 M NaCl pH 7.2 buffer to remove any excess uncoupled protein. Approximately 50-ml culture fluid was passed over the column. The column was washed with a Tris-NaCl buffer to remove any nonbound proteins that were trapped in the column. The proteins were then eluted from the column with 0.1 M glycine-HCl pH 2.8. The fractions were neutralized immediately. All fractions were assayed by ELISA to determine which fraction contained the maximum amount of colostrum associated SAA and also by western blot to assess the total protein content of the fractions. (FIG. 4).

Determining the amino acid sequence of the purified protein. The fraction containing the greatest amount of the colostrum-SAA was subjected to 12% SDS-PAGE and electroblotted onto a PVDF membrane by a Mini Trans-Blot system (BioRad Laboratories). A section of one lane of the membrane was cut off and was stained with the monoclonal antibody to SAA to verify the presence of the colostrum-SAA. The remainder of the membrane was stained for five minutes in a solution of methanol:water (40:60) containing 0.5% (wt/vol) Bromphenol Blue, and destained in a solution of methanol:water (50:50). The colostrum SAA proteins (identified by the monoclonal antibody stain) were excised from the membrane. The protein was deblocked using pfu pyroglutamate aminopeptidase (TaKaRa Biochemicals) followed by N-terminal sequencing using Edman degradation. Sequencing was performed on a Procise 491 made by PE-Biosystems through the University of Nebraska Medical Center's Protein Core Facility. The N-terminal sequence for colostrum-SAA was present (FIG. 5).

Isoelectric Focusing (IEF) of SAA from serum, colostrum and cell culture fluid. The PROTEIN IEF Cell (BioRad) was used for the isoelectric focusing of the various SAA preparations. Ready Strip IPG Strips (BioRad Laboratories) with a pH range of 3–10 were used for the IEF. The second dimension (2-D) of the protein analysis was done by subjecting the IPG strips to 12% SDS-PAGE gel and electroblotting onto a PVDF membrane. The strips and blots were done in duplicate so that one of the blots could be stained with a protein stain, Coomassie Brilliant Blue, (CBB) and the other stained with the anti-SAA monoclonal antibody for the identification of the SAA protein isoforms. The samples also contained internal IEF standards (BioRad Laboratories) so that isoelectric point (pI) of each SAA isoforms could be determined. By comparing the antibody stained spots to the spots of the standards stained with CBB the apparent pI of the SAA isoforms could be determined. All of these procedures were done according to the protocol recommended by the manufacturer.

The proteins subjected to the IEF and 2-D analysis were either affinity purified as described for the cell culture fluid or, in the case of the serum only semi-purified by hydrophobic chromatography. SAA is a highly hydrophobic molecule and will bind readily to Octyl Sepharose beads and then under the appropriate conditions can be eluted off the matrix. Briefly, serum with an elevated SAA level was tumbled for one hour with an equal volume of Octyl Sepharose CL-4B gel to allow for hydrophobic binding of the proteins from the serum to the gel. The gel was washed with Tris-HCl buffer to remove any proteins that were just trapped within the matrix. The proteins bound to the gel were eluted by 60% isopropanol in Tris-NaCl buffer. These eluates contain a variety of proteins of which about 20% is SAA. An aliquot of this preparation or the affinity purified Colostrum-SAA from the cell culture fluid or the colostrum was loaded onto the IPG strips and then standard procedures were followed for the IEF and the 2-D gel.

After analyzing the stained gels it was determined that the colostrum-SAA from both colostrum and MAC-T cell culture fluid had a pI of greater than 8 and was estimated to have an apparent pI of 9.4–9.6. The SAA from the serum contained of three isoforms with apparent pI values of approximately 7.0, 5.8 and 5.5. There was no isoform in the serum that matched the pI of the colostrum-SAA (FIG. 6).

EXAMPLE 6

Functional Roles of Colostrum-SAA

A remarkable feature of human physiology is that the mucosal epithelial cells that line the intestinal tract are in contact with a vast number of microbes and yet the incidence of infection and inflammatory complications is low. This suggests that local host protective mechanisms include highly effective, broad-spectrum, non-inflammatory antimicrobial defenses. Whereas the acquired immune system develops an effective response, it does so over a period of days or weeks and in infants the acquired immune system is immature and not fully functional. In contrast, the innate immune system of the intestinal tract is continual or immediately inducible to many potential pathogens introduced into the intestinal tract and brought into close proximity to the mucosal epithelial cells and functional at birth. Intestinal innate immunity includes first-line host-defense elements that range from simple inorganic molecules such as nitric oxide to natural killer cells. There are also a number of molecules produced by the epithelial cells that comprise an effector arm of the innate immune system. These include the relatively small antimicrobial peptides and more complex glycoprotein molecules such as mucins.

Mucins are secreted and cell-surface high-molecular-weight glycoproteins synthesized by epithelial cells of a number of organ systems including the intestinal tract. The strategic interpositioning between the intestinal lumen and the underlying mucosal epithelial cells of the intestinal tract has suggested that mucins have a number of important biological functions. In the intestinal tract, mucins protect against viral infections by inhibition of viral replication and enhancing viral clearance from the intestinal tract. Bacterial pathogens are prevented from adherence to intestinal epithelial cells. Adherence of enteropathogens is the crucial first step required for subsequent invasion, colonization or toxin delivery. Inhibition of adherence of enteric pathogens to intestinal epithelial cells by mucins could be by means of steric hindrance. Applicant's previous work and that of others has also shown that specific mucin-bacterial interactions could also be an important mechanism whereby mucins effect benefit for the host. However, regardless of the mechanism, prevention of mucosal infections is an important function of mucins.

Different mucin genes have been identified and to date, twelve human mucin genes have been identified. However, MUC3 mucin is the predominant intestinal mucin. It has previously been shown that the MUC3 mucins are effective in preventing the adherence of enteropathogenic *Escherichia coli* (EPEC) to intestinal epithelial cells. Applicant also showed that agents such as non-harmful bacteria that normally colonize the intestinal tract (i.e. probiotics) inhibit EPEC epithelial cell adherence and do so by the upregulation of intestinal mucin genes. It is also well known that breast-feeding infants are far less susceptible to infectious diarrhea than formula fed infants. There are a number of theories why this is so, but it is hypothesized that milk-associated amyloid (colostrum SAA) may be an important inducer of MUC3 gene expression. Applicant has evaluated MUC3 mRNA expression using an in vitro human cell culture assay system. In this system, intestinal cells incubated with the N-terminal peptide sequence of colostrum SAA have shown increased MUC3 mRNA expression as compared to control cells grown without the addition of colostrum SAA to the cell culture medium. To further explore this finding, Applicant has evaluated the functional specificity of the N-terminal peptide sequence of colostrum SAA by evaluation of MUC3 expression in the same in vitro assay using colostrum SAA N-terminal peptide sequences that have been randomly scrambled and a colostrum SAA peptide sequence downstream of the N-terminal sequence. If the expression of MUC3 is increased then intestinal cells grown in the presence of colostrum SAA should have a greater capacity to inhibit adherence of bacterial pathogens. This will be studied using EPEC in an in vitro assay system pre-incubated with colostrum SAA in the cell culture medium. Enteropathogenic *E. coli* are non-invasive, non-toxin producing pathogens that have been recognized as a significant cause of diarrhea in third world countries and in day care settings in developed countries. Future studies will evaluate the benefits of colostrum SAA in in vivo studies as well as characterized animal equivalent to human EPEC. Colostrum associated SAA provides a means to naturally upregulate the innate protective mechanisms of the human intestine and would provide a novel form of therapy to a common problem that occurs all too often in the third world leads to death of infants and in the developed world countries and leads to significant morbidity and cost. Furthermore, prevention of intestinal infections for traveler's or those having to live in conditions with altered sanitary practices would also reduce morbidity. Thus, this therapy offers an effective, natural, non-drug/chemical therapy.

In order to address possible functional roles of colostrum-SAA, the Applicant synthesized, on a standard amino acid synthesizer, a 10 amino acid region of the molecule from bovine that represented the N-terminal portion of the mature protein containing the conserved TFLK. The peptide consisted of the following amino acids: MWGTFLKEAG (SEQ ID NO:30) (Named "N-terminal"). Since it was anticipated that the TFLK amino acids would be the critical elements of the peptide, we also constructed a peptide in which those four amino acids were scrambled in their order MWGLTKFEAG (SEQ ID NO:28). (Named "Limited Scramble"). For controls we synthesized two peptides, one in which the amino acids in the entire N-Terminal peptide were arranged in random order GKFAWEGMTL (SEQ ID NO:29) (Named "Total Scramble") and a 10 amino acid peptide in which the first 7 residues were from the C-terminal region of bovine SAA DAAQRGPQQA (SEQ ID NO:33) (Named "C-terminal").

These four peptides were used in a cell culture assay designed to evaluate them for their properties of inducing mucin (MUC) mRNA production, either MUC3 or MUC2 according to the methods described by Mack et al. (Biochem. Biophys. Res. Commun. 199: 1012–1018, 1994 and Am J Physiol. Vol. 4, part 1, pg. G841–950, 1999).

Figure 7:
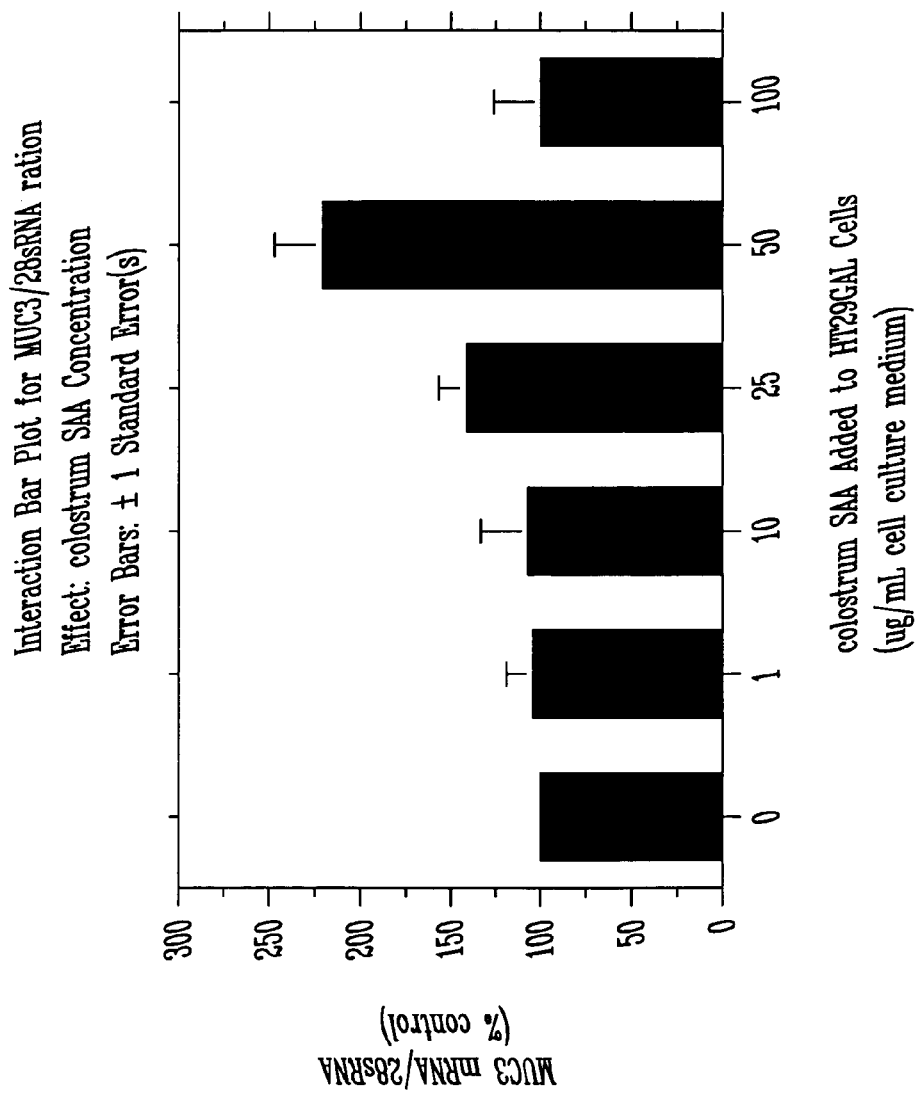
FIG. 7. N-Terminal Peptide Titration Mucin 3 (MUC3).

N-Terminal Peptide Titration and MUC3 mRNA Expression. Intestinal epithelial cells, Mack et al. 1994, 1999, were exposed to the N-terminal 10 amino acid bovine colostrum-SAA peptide (SEQ ID NO:30) at various concentrations for 30 minutes incubation at 370°C. The cells were incubated an additional hour following replacement of the test medium with fresh medium without peptide and then the total cellular niRNA isolated and analyzed for MUC3 specific mRNA. FIG. 7 shows that the N-terminal 10 amino acid, bovine Colostrum-SAA "N-terminal" peptide containing the TFLK motif stimulated the production of MUC3 mRNA up to 1½ times that of base line control levels (significance of P<0.0002). The optimum concentration was 50 µg/ml medium (see FIG. 7).

| | ANOVA Table for MUC3 mRNA/28sRNA ratio | | | | | | |
|---|---|---|---|---|---|---|---|
| | DF | Sum of Squares | Mean Square | F-Value | P-Value | Lambda | Power |
| colostrum SAA Concentration | 5 | 87931.344 | 17586.269 | 6.670 | .0002 | 33.349 | .996 |
| Residual | 37 | 97557.446 | 2636.688 | | | | |

| Means Table for MUC3 mRNA/28sRNA ratio Effect: Colostrum SAA Concentration | | | | |
|---|---|---|---|---|
| | Count | Mean | Std. Dev. | Std. Err. |
| 0 | 8 | 100.000 | 0.000 | 0.000 |
| 1 | 7 | 105.429 | 28.254 | 10.679 |
| 10 | 7 | 105.857 | 69.163 | 26.141 |
| 25 | 5 | 145.000 | 24.576 | 10.991 |
| 50 | 8 | 220.500 | 71.889 | 25.417 |
| 100 | 8 | 103.125 | 60.326 | 21.329 |

Figure 8:
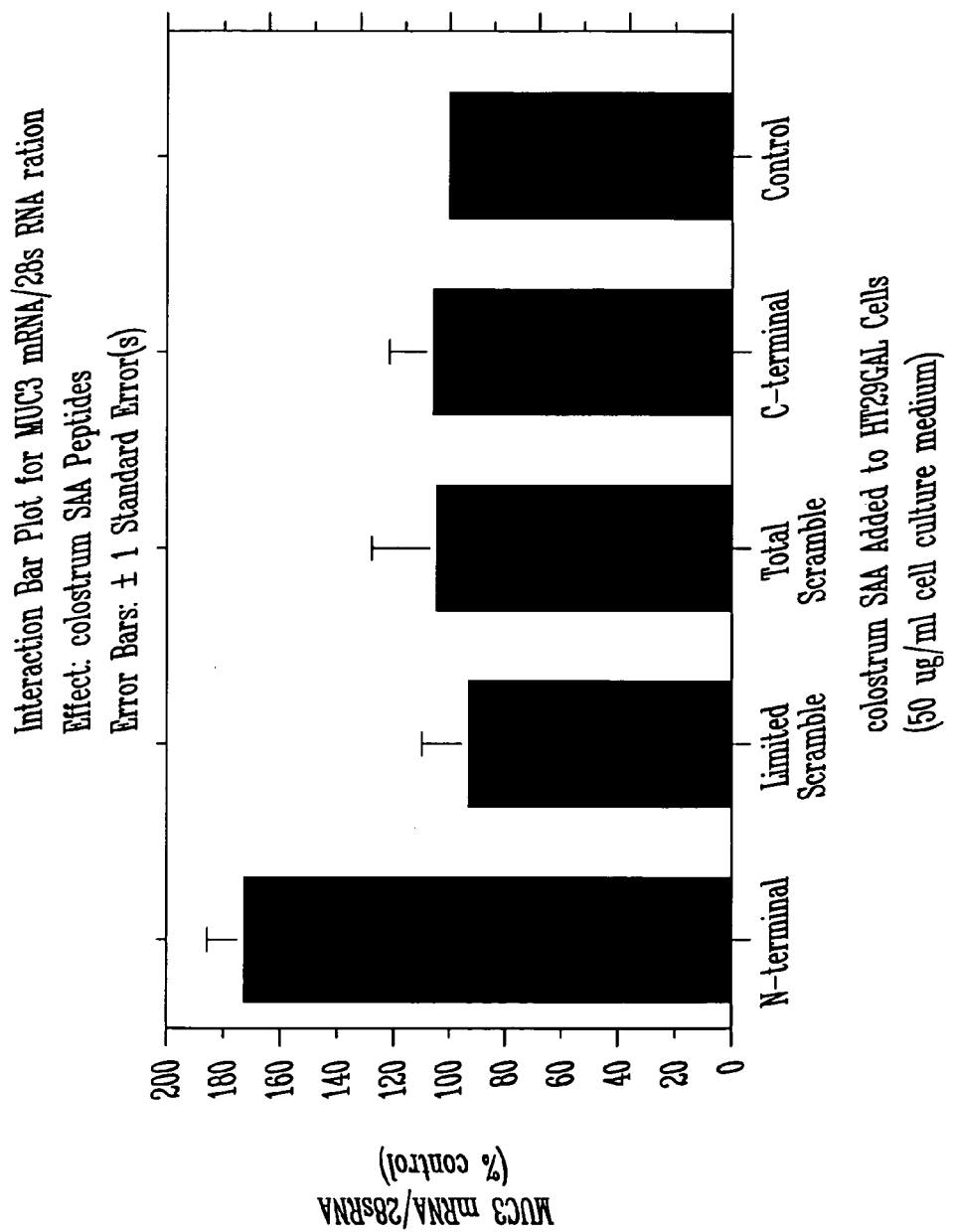
FIG. 8. Mucin 3 (MUC3) Stimulation.

MUC3 Stimulation. MUC3 stimulating activity of the N-terminal 10 amino acid bovine colostrum-SAA peptide was compared to the activity of the "Limited Scramble", the "Total Scramble" and "C-Terminal peptides". Optimum time and temperature of incubation and concentration of peptides was for 30 minutes at 37° C. at 50 µg/ml respectively. Data in FIG. 8 shows that the original N-Terminal peptide was the only peptide that stimulated MUC3 mRNA statistically significantly over the control values (p<0.008). Important note is that the lack of stimulation by the "Limited Scramble" peptide, in which only the novel TFLK sequence was rearranged strongly implies that this motif may be the key element in conferring biological activity and perhaps a rationale for it being conserved amongst species (see FIG. 8).

ANOVA Table for MUC2 mRNA/28s RNA ratio

|  | DF | Sum of Squares | Mean Square | F-Value | P-Value | Lambda | Power |
|---|---|---|---|---|---|---|---|
| Colostrum SAA Peptides | 4 | 6974.667 | 1743.667 | 5.081 | .0039 | 20.322 | .932 |
| Residual | 25 | 8580.000 | 343.200 | | | | |

Mean Table for MUC2 mRNA/28s RNA ratio
Effect: Colostrum SAA Peptides

|  | Count | Mean | Std. Dev. | Std. Err. |
|---|---|---|---|---|
| N-terminal | 6 | 101.167 | 21.876 | 8.931 |
| Limited Scramble | 6 | 87.167 | 24.078 | 9.830 |
| Total Scramble | 6 | 65.833 | 20.605 | 8.412 |
| C-terminal | 6 | 67.500 | 15.268 | 6.233 |
| Control | 6 | 100.000 | 0.000 | 0.000 |

Figure 9:
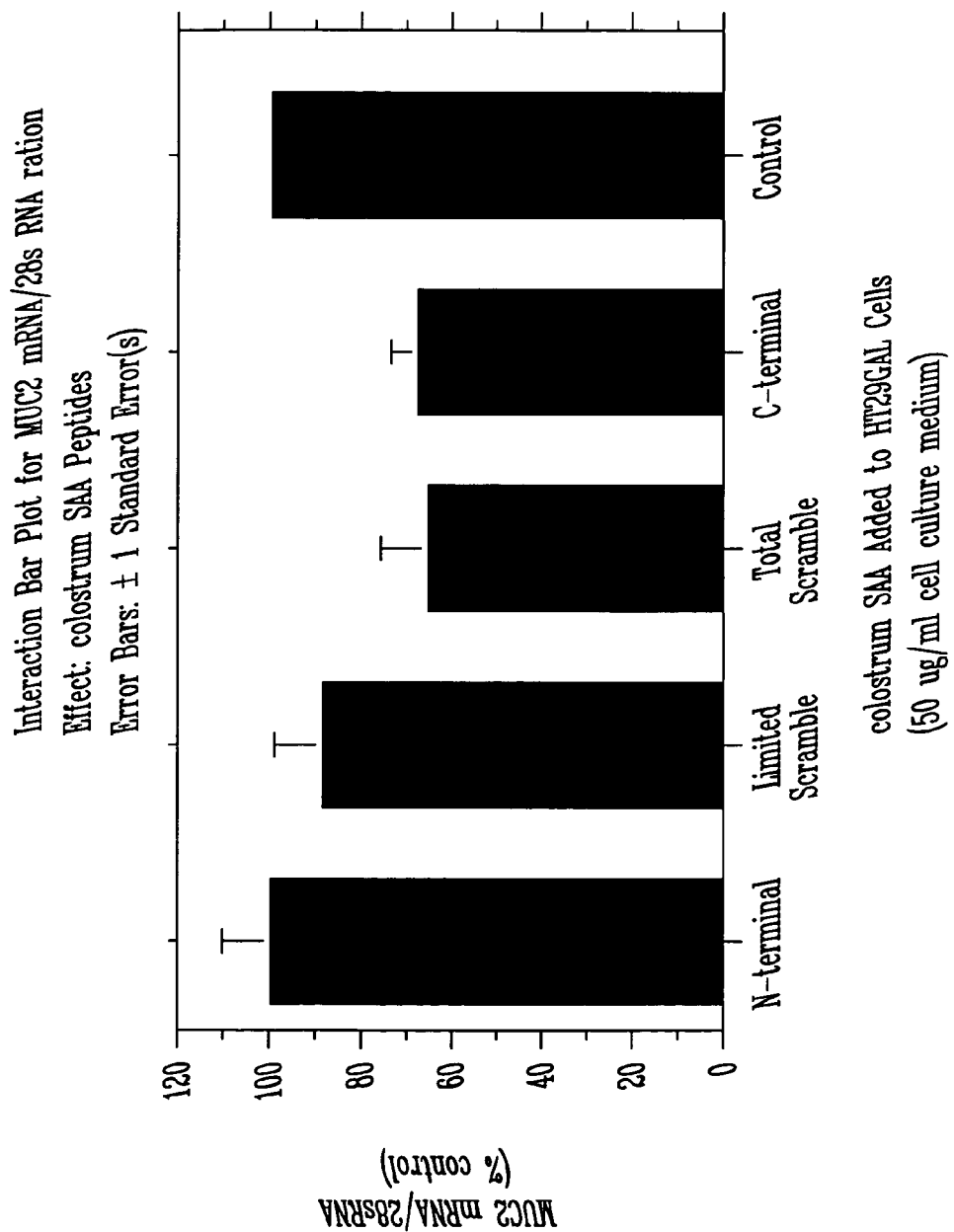
FIG. 9. Mucin 2 (MUC2) Stimulation.

MUC2 mRNA Stimulation. To address whether the N-Terminal 10 amino acid bovine colostrum-SAA peptide would stimulate mRNA synthesis for MUC2 production, intestinal epithelial cells were cultured under conditions favoring MUC2 expression rather than MUC3. All peptides were used at concentrations and conditions that were previously optimized for MUC3 stimulation. As shown in FIG. 9, none of the peptides stimulated the production of MUC2 mRNA. When comparing the N-Terminal 10 amino acid peptide that stimulated MUC3 to control baseline levels, the values were not significantly different. To show that the lack of MUC2 stimulation was not due to culture conditions, cells were exposed to the N-Terminal 10 amino acid bovine colostrum-SAA peptide at 2× and 5× optimum levels for MUC3 (100 and 500 μg/ml respectively). Additionally, conditions were changed to 2× the optimum MUC3 incubation time (1 hr). None of these changes resulted in MUC2 mRNA increase over control values. The evidence strongly indicates specificity of function in stimulating the production of a mucin produced mainly in the small intestine (MUC3) over one produced primarily in the large intestine (MUC2) (see FIG. 9).

ANOVA Table for MUC3 mRNA/28s RNA ratio

|  | DF | Sum of Squares | Mean Square | F-Value | P-Value | Lambda | Power |
|---|---|---|---|---|---|---|---|
| Colostrum SAA Peptides | 4 | 25215.200 | 6303.800 | 4.387 | .0080 | 17.550 | .886 |
| Residual | 25 | 35919.500 | 1436.780 | | | | |

Mean Table for MUC3 mRNA/28s RNA ratio
Effect: Colostrum SAA Peptides

|  | Count | Mean | Std. Dev. | Std. Err. |
|---|---|---|---|---|
| N-terminal | 6 | 174.833 | 22.266 | 9.090 |
| Limited Scramble | 6 | 95.000 | 38.063 | 15.539 |
| Total Scramble | 6 | 109.333 | 56.874 | 23.219 |
| C-terminal | 6 | 111.333 | 44.774 | 18.279 |
| Control | 6 | 100.000 | 0.000 | 0.000 |

The present invention is not limited to the embodiments described above, but is capable of modification within the scope of the appended claims.

EXAMPLE 7

Colostrum-SAA Production by Bovine MAC-T Mammary Epithelial Cells after Stimulation of by Lipopolysaccharide (LPS)

Figure 11:
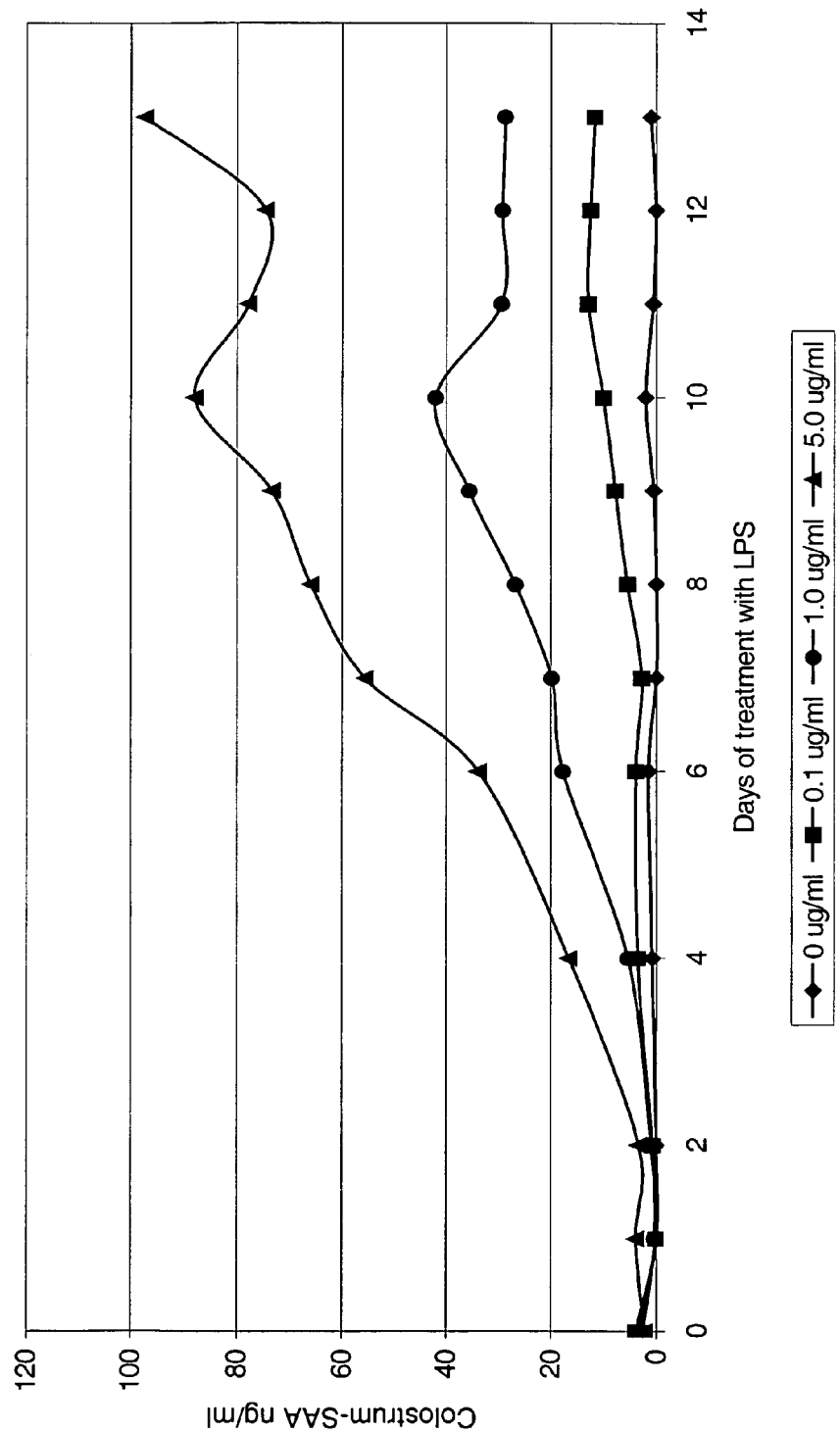
FIG. 11. is a graph showing the production of colostrum-SAA by the MAC T bovine epithelial cells over a periods of 13 days of stimulation with different levels of lipopolysaccharide (LPS). Measurable quantities of colostrum-SAA could be detected by day 1 when the cells were stimulated with LPS at 5 μg/ml.

Bovine MAC-T mammary gland epithelial cells were obtained from ATCC (CRL-10274) and cultured according to recommended conditions (Immortalized bovine mammary epithelial cell line. U.S. Pat. No. 5,227,301 dated Jul. 13,1993). MAC-T cells were cultured on Dulbecco's Modified Eagles Media (DMEM) supplemented with 10% Fetal Calf Serum (FCB), 5 ug/ml insulin, 1 ug/ml hydrocortisone and fungizone. Cells were incubated at 37°C. with 5% $CO_2$. Typically, for colostrum-SAA production the cells were seeded at $2.5 \times 10^5$ cells/$cm^2$ onto type I Collagen coated plates. After 14 hours of incubation, the cells were washed twice with Dulbecco's phosphate buffered saline (DPBS) and incubated with media (DMEM, 5 ug/ml insulin, 1 ug/ml hydrocortisone and 2.5% FCS) supplemented with lipopolysaccharide from E. coli. The concentration of LPS added to the media for the stimulation of colostrum-SAA production ranged from 0 to 5 μg/ml. Essentially all of the media was replaced daily with fresh LPS supplemented media. Standard ELISA for the quantitation of SAA (FIG. 11) was used to assay aliquots of growth media collected daily for the presence of the colostrum-SAA.

For the production of colostrum-SAA, the cells could also be cultured on regular tissue culture plates (non-collagen coated). Cells were kept in culture for 40 days on these plates in media supplemented with LPS at 10 µg/ml with a daily replacement of the media. Levels of colostrum-SAA production reached a maximum of almost 30 µg/ml.

Aliquots of the culture fluid from the MAC-T cells collected at various times over the period of 27 days were analyzed for protein content. The proteins from these samples were separated by SDS-PAGE on a 10% gel and then silver stained. The protein profile changed over the period of 27 days. Although the individual proteins were not identified, changes in overall banding patterns could be observed, particularly between the molecular weight range of 15–25 kDa. Here, several proteins could be detected by day 3 but then were no longer detectable by day 18. The production of colostrum-SAA, as determined by ELISA since on the gel SAA was obscured by the heavy band at 15 kDa, increased in concentration from 0.001 µg/ml on day 1 to approximately 25 µg/ml by day 27.

Purification of Colostrum-Associated SAA from Cell Culture Fluid. Colostrum-SAA was purified from cell culture fluid by affinity chromatography. Briefly, an affinity column was prepared by coupling monoclonal antibody with specificity to SAA to cyanogen bromide activated sepharose 4B. Treating the column with 50 mM Tris, 0.1 M NaCl, 0.2 M glycine pH 8 buffer blocked residual active groups on the gel. The column was then washed with 50 mM Tris, 0.1 M NaCl pH 7.2 buffer to remove any excess uncoupled protein. Approximately 50 ml culture fluid was passed over the column. The column was then washed with the Tris-NaCl buffer to remove any non-bound proteins that were trapped in the column. A 0.1 M glycine-HCl pH 2.8 buffer was used to elute the proteins from the column. The fractions were neutralized immediately. All fractions were assayed by ELISA to determine which fractions contained the maximum amount of colostrum associated SAA.

Isoelectric Focusing (IEF) of SAA from Colostrum and Cell Culture Fluid. The PROTEIN IEF Cell (BioRad) was used for the isoelectric focusing of the SAA preparations. Since both colostrum and media from MAC-T cells stimulated by prolactin contain the same isoform, only the SAA purified form colostrum was used for the comparison. The samples of SAA had been prepared by affinity purification. Ready strip IPG Strips (BioRad Laboratories) with a pH range of 3–10 and 7–10 were used for the IEF. The second dimension (2-D) of the protein analysis was done by subjecting the IPG strips to 12% SDS-PAGE gel and electroblotting onto a PVDF membrane. The blots were stained with anti-SAA antibody for the identification of the SAA protein isoforms. By comparing the spots stained with the antibody on the blot of the 2D gel from the SAA purified from colostrum and the SAA from the culture fluid of MAC-T cells stimulated with LPS, the similarities of the isoforms could be determined. Each sample was first analyzed on a pH 3–10 IPG strip for the first dimension of separation and then a subsequent sample analyzed on a pH 7–10 IPG strip.

After analyzing the stained gels it was determined that the SAA purified from the culture fluid of MAC-T cells stimulated with LPS contains only one isoform of SAA with the pI of 9.4–9.6. This is identical to the pI of the SAA purified from colostrum and not to the isoforms associated with the acute phase response. (FIG. 4). LPS is a compound that normally elicits an inflammatory response. SAA that is produced by the MAC-T cells as a result of LPS stimulation is the same as the colostrum SAA produced as a result of hormonal (prolactin) stimulation of the MAC-T cells and also the same isoform that is present in colostrum.

EXAMPLE 8

Bovine Colostrum Serum Amyloid A 3 Genomic Sequence

Cloning Of Sequence Identification No. 13: The cDNA and amino acid sequence for bovine M-SAA3 (MAA) was obtained as previously described herein and has been deposited in the GenBank database under Accession No. AF335552. The nucleotide sequence of the introns, promoter, and 3' flanking regions for the bovine M-SAA3 gene were determined by PCR amplification and genomic walking procedures (Universal Genome Walker Kit; Clontech). The primary and nested secondary M-SAA3 gene-specific primers used in the genomic walking procedures were designed according to the manufacturer's recommendations and were initially complimentary to either the 5' or 3' region of the bovine M-SAA3 cDNA previously described. Primary PCRs were carried out in 25 µL volumes containing 200 µM of adapter primer (AP1), 200 µM deoxynucleoside triphosphates, 1.1 mM magnesium acetate, 15 mM potassium acetate, 40 mM Tris-HCl (pH 9.3), 1 U of rTth DNA polymerase XL (Perkin-Elmer), and approximately 25 ng of adapter-ligated bovine genomic DNA digested with either StuI, ScaI, HincIII, or SspI. The thermal cycling parameters used were 7 cycles for 15 seconds at 94° C. and 3 minutes at 72° C., 37 cycles for 15 seconds at 94° C. and 3 minutes at 67° C., and then 1 cycle for 4 minutes at 67° C. Secondary PCRs were carried out in 50 µL volumes containing 1 µL of a 1:50 dilution of the appropriate primary PCR mixture, adapter primer AP2, and either a forward or reverse nested M-SAA3 gene-specific primer. The other reaction components and thermal cycling parameters were the same as those used for primary PCR.

Nucleotide Sequencing And Computer Analysis Of Genomic Sequence: The resulting 2.4 kb StuI, 1.7 kb Seal, 1.8 kb HincII, and 1.5 kb SspI secondary PCR products obtained from genomic walking, in addition to PCR products obtained using primer-walking methodology, were sequenced by the DNA Sequencing Facility at either Iowa State University or at the University of Nebraska Medical Center using the AP2 primer and/or M-SAA3 gene-specific primers. The DNA sequence from several independent high-fidelity PCR products was analyzed using the Wisconsin Genetics Computer Group (GCG) Package (Version 10.1, Madison, Wis.). Assembly of the overlapping amplicons provided the following nucleotide sequence for the TATA box, exons, introns, and 3' flanking region of the bovine M-SAA3 gene (SEQ ID NO: 31) See FIG. 10. The TATA box is double underlined in the promoter region for bovine mammary-associated serum amyloid A 3 (M-SAA3, MAA). The additional three upstream nucleotides (single underlined) from the TATA box are also conserved in most "milk protein" TATA boxes. The transcriptional start site is underlined and indicated above the nucleotide with +1. The beginning and ending of the three introns are denoted with an arrow above these regions. The start and stop colons are underlined and indicated above the nucleotides. The encoded amino acids are denoted under the double-stranded DNA sequence. The presumed signal peptide cleavage site to remove the leader sequence predicted by the SignalP Program (Version 1.1) (Nielsen et al., 1997) with 100% certainty is denoted by an inverted triangle. The polyadenylation signal (3773 to 3778) is underlined and the probable site for cleavage and polyadenylation is indicated with a double arrow.

REFERENCES

Nielsen H., Engelbrecht J., Brunak S., von Heijne G. 1997. Identification of prokaryotic and eukaryotic signal peptides and prediction of their cleavage sites. Protein Engineering 10:1–6.

Quandt K., Frech K., Karas H., Wingender E., Werner T. 1995. MatInd and MatInspector—New fast and versatile tools for detection of consensus matches in nucleotide sequence data. Nucleic Acids Research 23:4878–4884.

We claim:

1. A purified and isolated nucleic acid molecule that encodes colostrum associated serum amyloid A (SAA) protein comprising the TFLK amino acid sequence depicted in SEQ ID NO: 34, wherein said nucleic acid molecule comprises one or more non-coding regions from SEQ ID NO: 31.

2. The nucleic acid molecule of claim 1 wherein said molecule is purified and isolated from bovine species.

3. The nucleic acid molecule of claim 1 wherein said non coding region is 5' of base 648 in SEQ ID NO: 31.

4. The nucleic acid molecule of claim 1 wherein said non-coding region consists of bases 739 to 2982 of SEQ ID NO: 31 or the complement thereof.

5. The nucleic acid molecule of claim 1 wherein said non-coding region consists of bases 3122 to 3510 of SEQ ID NO: 31 or the complement thereof.

6. The nucleic acid molecule of claim 1 wherein said non-coding region consists of bases 3674 to 4984 of SEQ ID NO: 31 or the complement thereof.

7. An expression cassette which comprises the nucleic acid molecule of claim 1 operably linked to a promoter region.

8. A cloning or expression vector comprising the expression cassette of claim 7.

9. An expression cassette which comprises the nucleic acid molecule of claim 8 operably linked to a promoter nucleotide.

10. The nucleic acid molecule of claim 1 wherein said TFLK amino acid sequence depicted in SEQ ID NO: 34 is located within amino acids 1–26 at the N-terminal region of said protein.

11. A purified and isolated nucleic acid molecule that encodes colostrum associated serum amyloid A (SAA) protein comprising the TFLK amino acid sequence depicted in SEQ ID NO: 34 , wherein said nucleic acid molecule encodes the peptide of SEQ ID NO:3 or SEQ ID NO: 4 and one or more of a sequence selected from the group consisting of SEQ ID NO: 5, SEQ ID NO: 6,SEQ ID NO: 7 and SEQ ID NO: 8.

12. A purified and isolated genomic bovine nucleotide sequence which encodes colostrum associated serum amyloid A (SAA) protein said sequence comprising a non-coding region selected from the group consisting of bases 1–647, 739–2982, 3122–3510, 3674–4984 of SEQ ID NO: 31 or the complement thereof.

13. A eucaryotic or procaryotic host cell transformed with a vector comprising the nucleotide sequence of claim 12.

14. A purified and isolated nucleic acid molecule that encodes colostrum associated serum amyloid A (SAA) comprising the TFLK amino acid sequence depicted in SEQ ID NO:34, wherein said nucleic acid molecule comprises SEQ ID NO: 31.

15. A eucaryotic or procaryotic host cell transformed with a vector comprising the nucleic acid molecule of claim 14.

16. The nucleic acid molecule of claim 14 wherein said TFLK amino acid sequence depicted in SEQ ID NO: 34 is located within amino acids 1–26 at the N-terminal region of said protein.

17. A method for producing mammary-associated serum amyloid A 3 (MAA) peptide comprising:
   administering a MAA inducing agent to a bovine mammary epithelial cell line;
   culturing said cell so that MAA is produced;
   harvesting said MAA from said mammary epithelial cell; and
   purifying said MAA from said cell.

18. A bovine mammary-associated serum amyloid A 3 (MAA) peptide produced by the method of claim 17.

19. A method for producing mammary-associated serum amyloid A 3 (MAA) peptide comprising:
   administering a MAA inducing agent to a bovine mammary epithelial cell line;
   culturing said cell so that MAA is secreted from said cell;
   harvesting said MAA from said mammary epithelial cell culture; and
   purifying said MAA from said cell culture.

20. A bovine mammary-associated serum amyloid A 3 (MAA) peptide produced by the method of claim 19.

* * * * *